United States Patent
Zhang et al.

(10) Patent No.: US 10,092,543 B2
(45) Date of Patent: Oct. 9, 2018

(54) METHODS OF TREATING AUTOIMMUNE AND/OR GLOMERULONEPHRITIS-ASSOCIATED DISEASES USING SHP2 INHIBITORS

(71) Applicants: Indiana University Research and Technology Corporation, Indianapolis, IN (US); Beth Israel Deaconess Medical Center, Inc., Boston, MA (US)

(72) Inventors: Zhong-Yin Zhang, Carmel, IN (US); Maria Kontaridis, Auburndale, MA (US); Li-Fan Zeng, Indianapolis, IN (US); Jianxun Wang, Cambridge, MA (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/813,729

(22) Filed: Nov. 15, 2017

(65) Prior Publication Data

US 2018/0071252 A1    Mar. 15, 2018

Related U.S. Application Data

(62) Division of application No. 14/902,485, filed as application No. PCT/US2014/045318 on Jul. 2, 2014, now Pat. No. 9,844,535.

(60) Provisional application No. 61/842,813, filed on Jul. 3, 2013.

(51) Int. Cl.
*A61K 31/404* (2006.01)
*A61K 31/427* (2006.01)
*A61K 31/4178* (2006.01)
*A61K 31/433* (2006.01)
*A61K 31/428* (2006.01)
*A61K 31/4184* (2006.01)
*A61K 31/4025* (2006.01)

(52) U.S. Cl.
CPC ........ *A61K 31/404* (2013.01); *A61K 31/4025* (2013.01); *A61K 31/4178* (2013.01); *A61K 31/4184* (2013.01); *A61K 31/427* (2013.01); *A61K 31/428* (2013.01); *A61K 31/433* (2013.01)

(58) Field of Classification Search
CPC ........................... A61K 31/404; A61K 31/405
See application file for complete search history.

(56) References Cited

FOREIGN PATENT DOCUMENTS

| WO | 2004060878 A2 | 7/2004 |
|---|---|---|
| WO | 2004062664 A1 | 7/2004 |
| WO | 2005108661 A2 | 11/2005 |

(Continued)

OTHER PUBLICATIONS

Grammatilos, et al., A T cell gene expression panel for the diagnosis and monitoring of disease activity in patients with systemic lupus erthematosus, Clin Immunol., Feb. 2014; vol. 150 (2): pp. 192-200.

(Continued)

*Primary Examiner* — San Ming R Hui
(74) *Attorney, Agent, or Firm* — Stinson Leonard Street LLP

(57) ABSTRACT

Methods are disclosed herein for administering a oncogenic Src homology-2 domain containing protein tyrosine phosphatase-2 (SHP2) inhibitor for treating autoimmune and/or glomerulonephritis-associated diseases, and in particular, Systemic Lupus Erythematosus (SLE).

13 Claims, 39 Drawing Sheets

(56) References Cited

FOREIGN PATENT DOCUMENTS

WO 2012149048 A1 11/2012
WO 2014176488 A1 10/2014

OTHER PUBLICATIONS

Kontaridis, et al., PTPN11 (shp2) Mutations in LEOPARD Syndrome Have Domiant Negative, Not Activating, Effects, The Journal of Biological Chemistry, vol. 281, No. 10, pp. 6785-6792, Mar. 10, 2006.

Marin, et al., Rapamycin reverses hypertrophic cardiomyopathy in a mouse model of LEOPARD syndrome-associated PTPN11 mutation, The Journal of Clinical Investigation, vol. 121, No. 3, Mar. 2011, pp. 1026-1043.

Wang, et al., Inhibition of SHP2 ameliorates the pathogenesis of systemic lupus erythematosus, The Journal of Clinical Investigation, 2016, vol. 126, No. 6, pp. 2077-2092.

Zeng, et al., Therapeutic Potential of Targeting the Oncogenic SHP2 Phosphatase, Journal of Medicinal Chemistry, 2014, vol. 57, pp. 6594-6609.

Zeng, et al., Hydroxyindole Carboxylic Acid-Based Inhibitors for Receptor-Type Protein Tyrosine Protein Phosphatase Beta, Antioxidants & Redox Signaling, 2014, vol. 20, No. 14, pp. 2130-2140.

-8-wk-old female mice

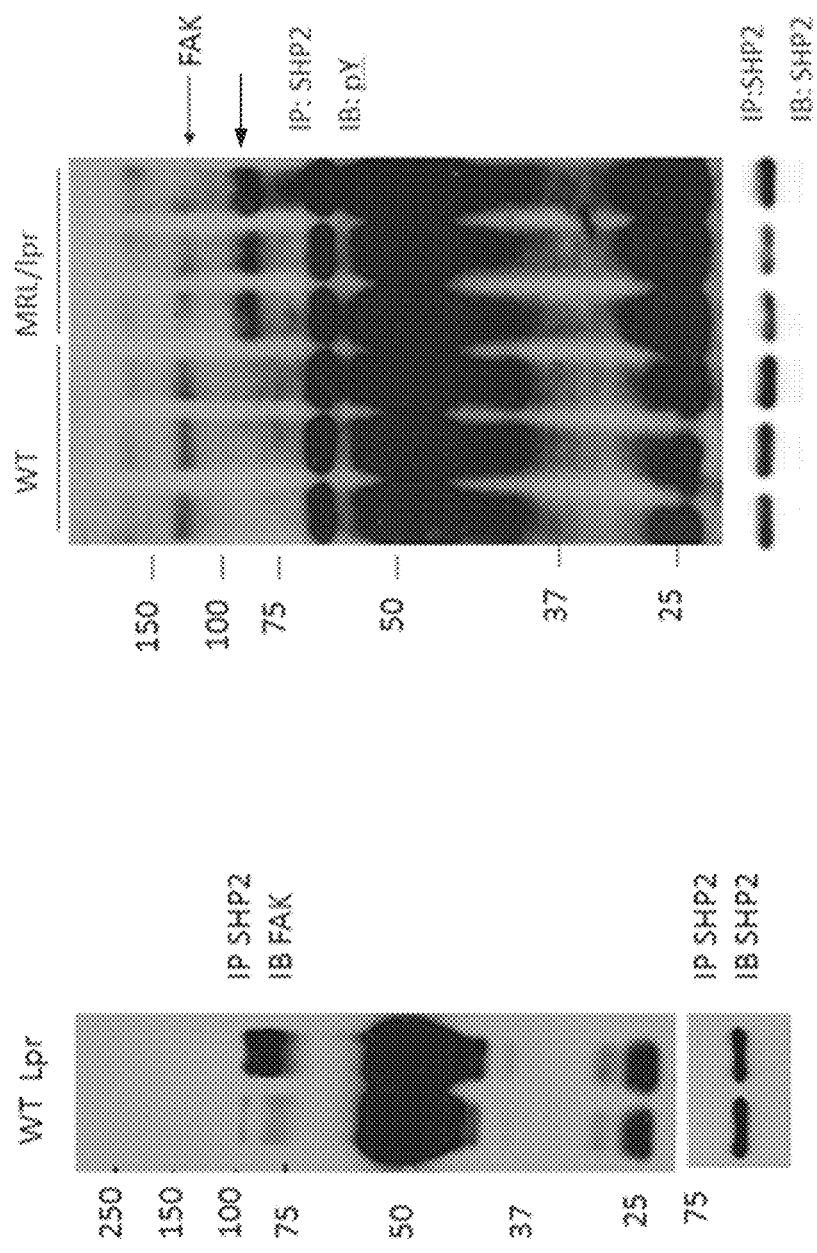

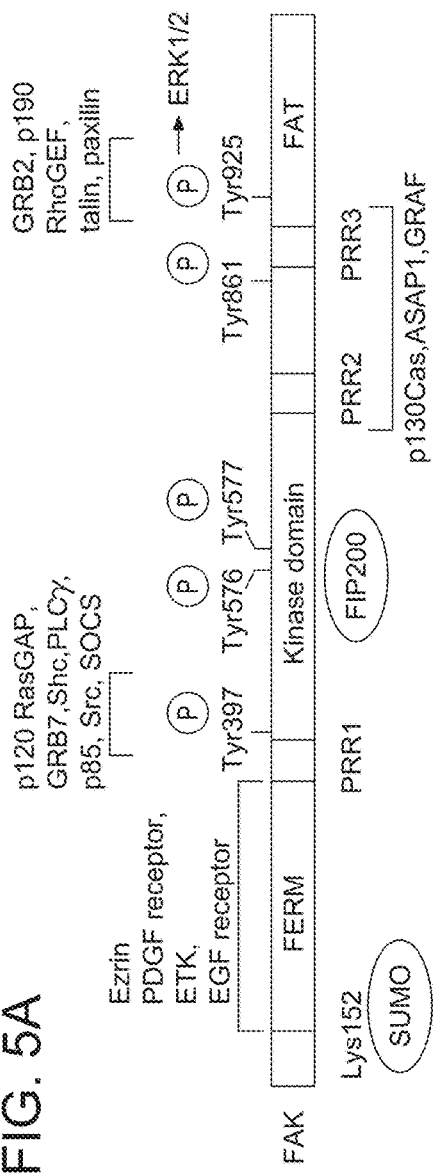
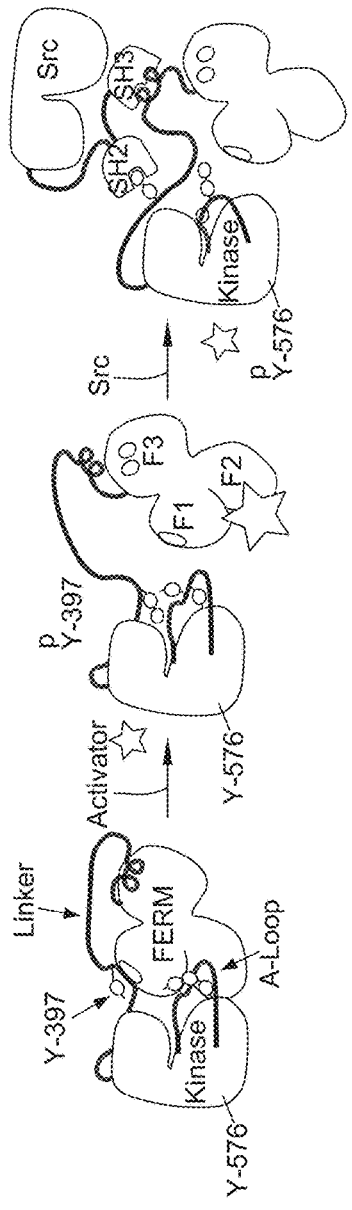
FIG. 5A
FIG. 5B

*, p<0.01, B6WT vs. MRL/lpr by T-test, n=3 each group

*, p<0.01, B6WT vs. MRL/lpr by T-test and #, p<0.05, MRL/lpr 8w vs. MRL/lpr 16w by two way Anova, n=3 each group

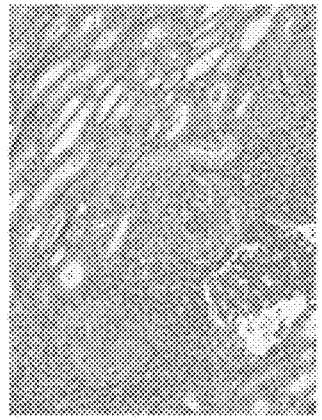
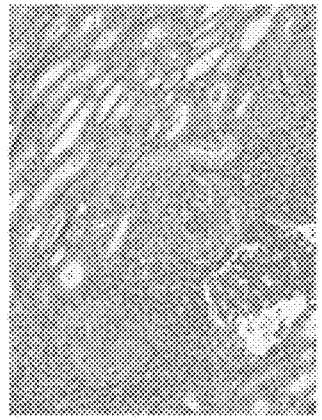
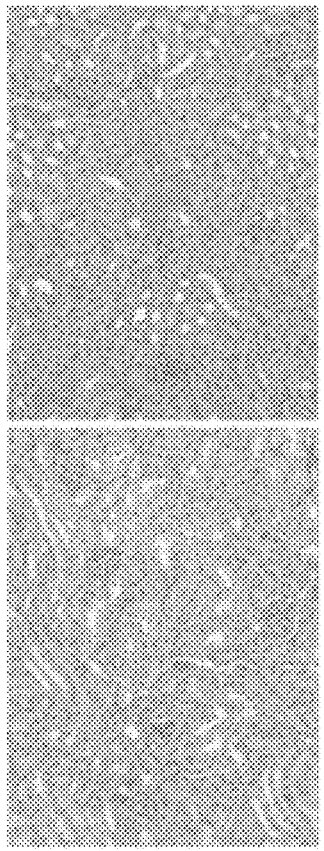
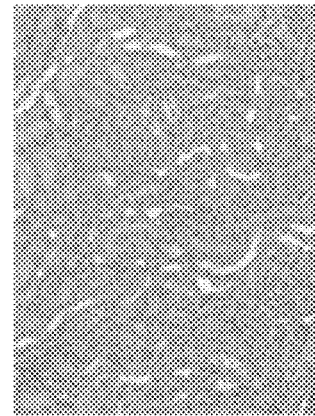
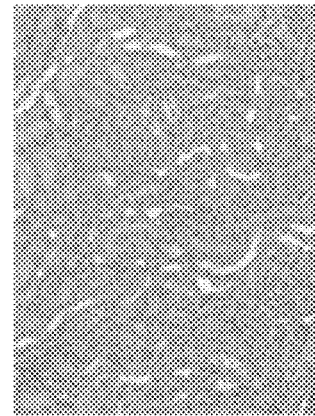
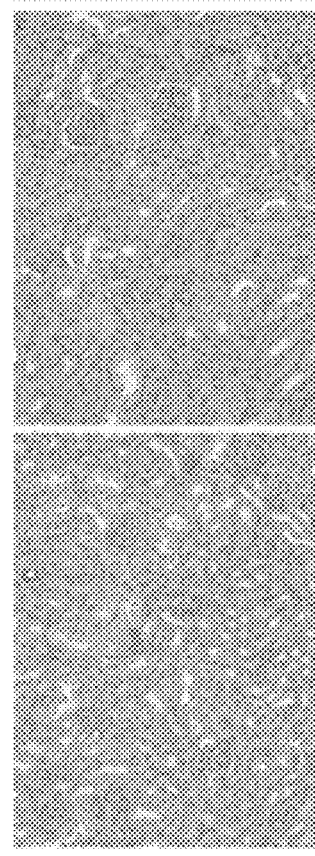
FIG. 14A WT DMSO
FIG. 14B MpJ DMSO
FIG. 14C lpr DMSO
FIG. 14D WT Inhibitor
FIG. 14E MpJ Inhibitor
FIG. 14F lpr Inhibitor

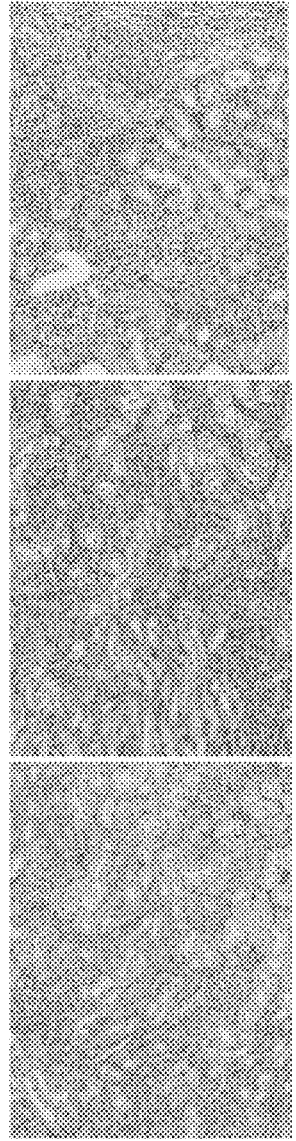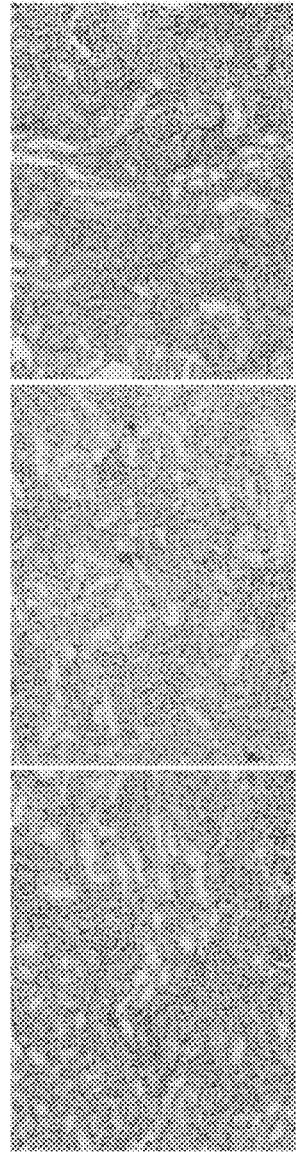

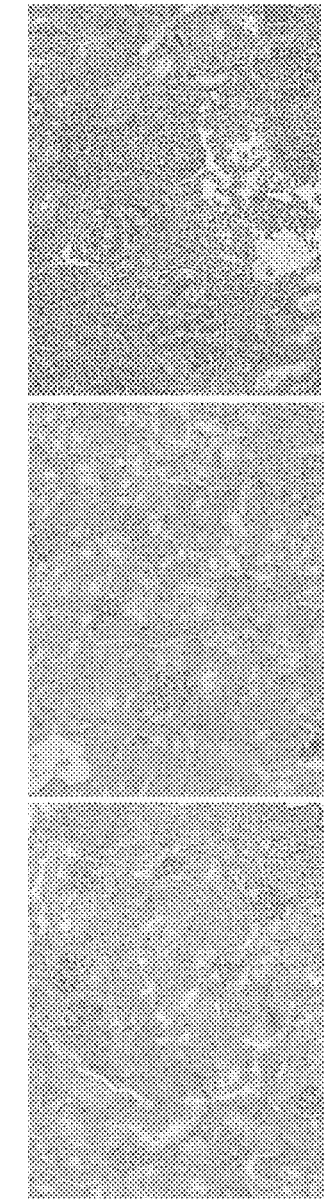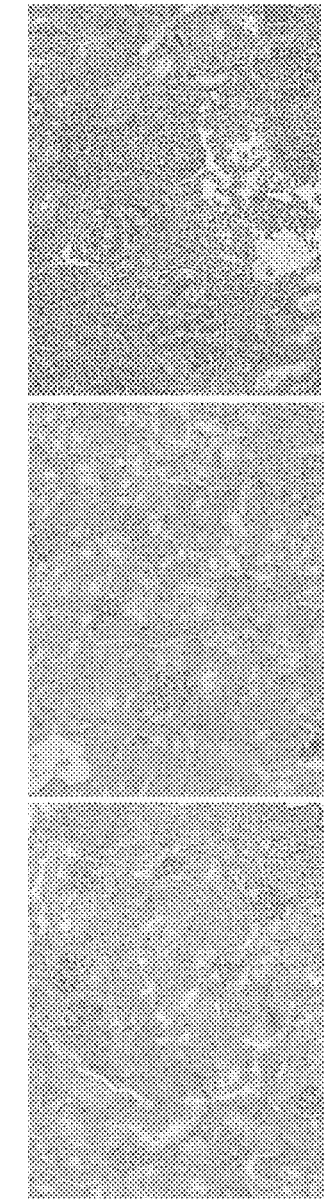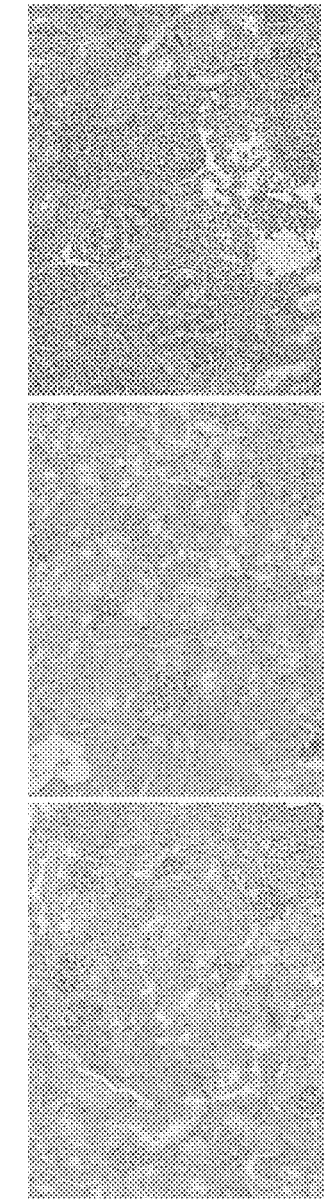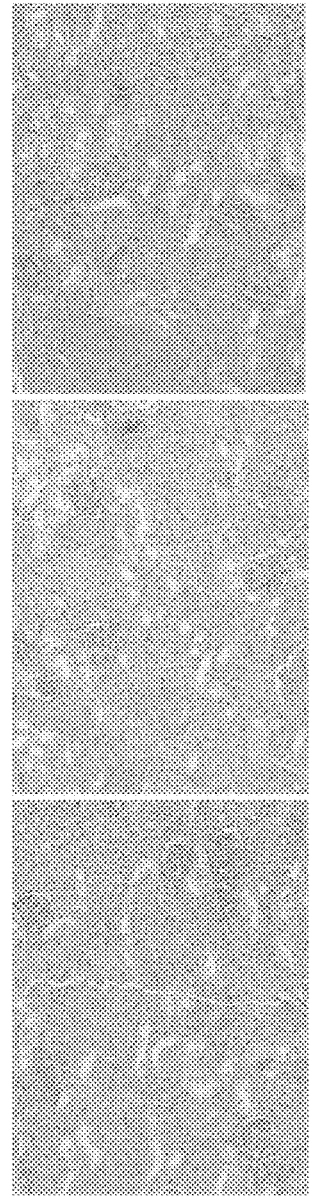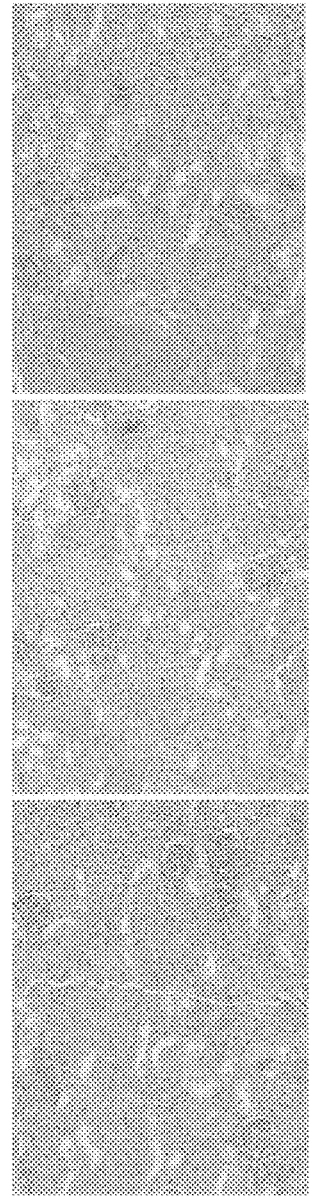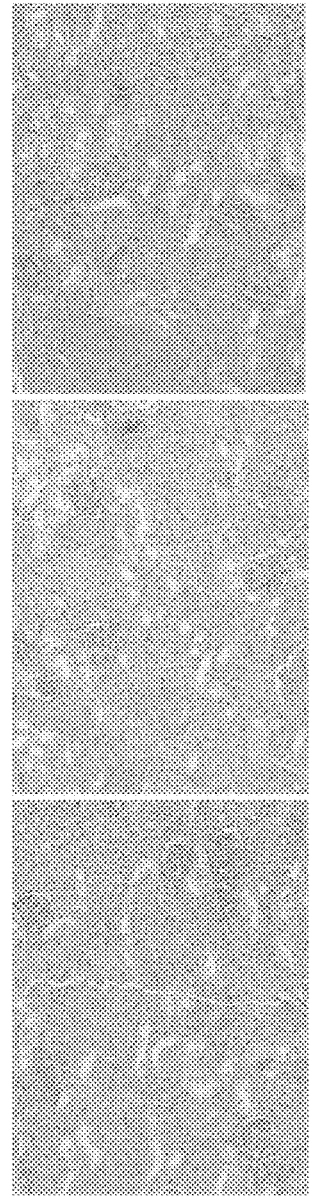
FIG. 16A WT DMSO  FIG. 16B MpJ DMSO  FIG. 16C lpr DMSO
FIG. 16D WT Inhibitor  FIG. 16E MpJ Inhibitor  FIG. 16F lpr Inhibitor FIG. 18A  FIG. 18B
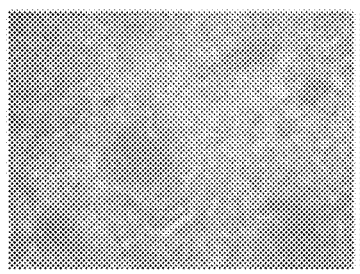 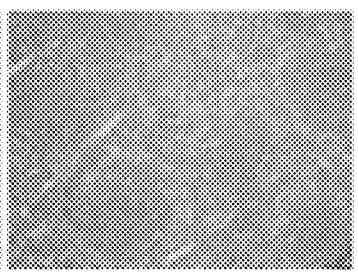
B6WT  MRL/MpJ
HE staining for spleens
FIG. 18C  FIG. 18D
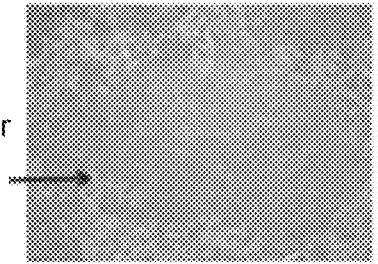 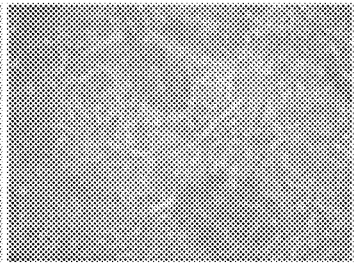
MRL/lpr  MRL/lpr_Tx
HE staining for spleens

THYMUS

| | 12w | | 13w | | 14w | | 15w | | 16w | |
| --- | --- | --- | --- | --- | --- | --- | --- | --- | --- | --- |
| | lpr | lpr+Tx | lpr | lpr+Tx | lpr | lpr+Tx | lpr | lpr+Tx | MpJ | lpr | lpr+Tx |
| LVEDd (mm) | 3.87 | 3.51 | 3.82 | 3.69 | 3.85 | 3.62 | 3.93 | 3.62 | 3.30 | 4.02 | 3.60 |
| LVPWd (mm) | 1.23 | 1.17 | 1.29 | 1.11 | 1.19 | 1.23 | 1.19 | 1.21 | 1.29 | 1.12 | 1.27 |
| FS% | 69.4 | 70.0 | 66.3 | 69.0 | 64.3 | 70.3 | 66.0 | 72.4 | 78.0 | 65.0 | 74.6 |

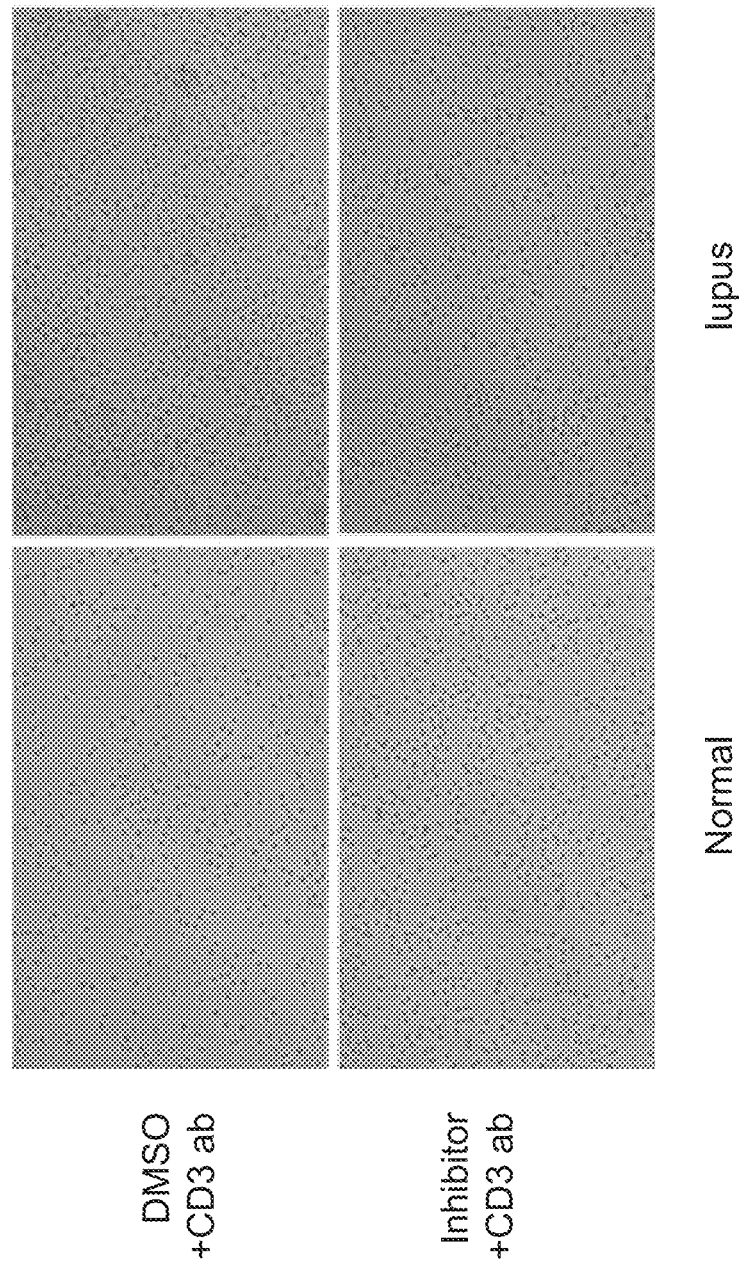

METHODS OF TREATING AUTOIMMUNE AND/OR GLOMERULONEPHRITIS-ASSOCIATED DISEASES USING SHP2 INHIBITORS

CROSS-REFERENCE TO RELATED APPLICATIONS

This application is a divisional application of U.S. patent application Ser. No. 14/902,485, filed on Dec. 31, 2015, which claims priority to International Publication Number WO 2015/003094, filed on Jul. 2, 2014, which claims priority to U.S. Provisional Patent Application No. 61/842,813, filed on Jul. 3, 2013, the disclosures of which are incorporated by reference in their entireties.

STATEMENT REGARDING FEDERALLY SPONSORED RESEARCH & DEVELOPMENT

This invention was made with government support under HL102368, HL114775, and CA152194 awarded by the National Institutes of Health. The Government has certain rights in the invention.

BACKGROUND OF THE DISCLOSURE

The field of the disclosure relates generally to a potent and specific oncogenic Src homology-2 domain containing protein tyrosine phosphatase-2 (SHP2) inhibitor and to methods of administering the inhibitor for treating autoimmune diseases, and in particular, to treating glomerulonephritis-associated diseases such as systemic lupus erythematosus (SLE).

Systemic lupus erythematosus (SLE), a multi-systemic autoimmune disease with a prevalence in about 40-200/100,000 persons, is thought to be caused by multiple pathogenic responses, including genetic, environmental, hormonal, epigenetic, and immunoregulatory factors, that either sequentially or simultaneously affect the immune system. Action of these pathogenic factors results in generation of autoantibodies, immune complexes, autoreactive or inflammatory T cells, and inflammatory cytokines that, together, lead to amplification of inflammatory signaling pathways and damage to vital organs (e.g., skin, kidneys, spleen, heart, thymus, lymph nodes, joints, and nervous system).

Cytokines such as IL-6, IL-4, IL-5 and IL-10 are overproduced in lupus patients. Aberrant regulation of cytokines, such as IL-6, IL-10, IL-17, type I interferon (IFN) and tumor necrosis factor-α (TNF-α), are closely linked to pathogenesis of SLE, playing key roles in the regulation of systemic inflammation, local tissue damage, and immunomodulation. However, the specific signaling mechanisms that cause SLE remain elusive and current therapeutic strategies primarily target the symptoms and not the disease itself.

Accordingly, there is a continuing need for new therapeutic compounds and methods of treating glomerulonephritis-associated diseases such as SLE.

BRIEF DESCRIPTION OF THE DISCLOSURE

The present disclosure is generally directed to methods of administering potent and specific oncogenic Src homology-2 domain containing protein tyrosine phosphatase-2 (SHP2) (also known as protein tyrosine phosphatase, non-receptor type 11 (PTPN11)) inhibitors. More particularly, the disclosure is directed to administering the SHP2 inhibitors to treat glomerulonephritis-associated diseases, and in particular, Systemic Lupus Erythematosus (SLE).

Accordingly, in one embodiment, the present disclosure is directed to a method for inhibiting specific oncogenic Src homology-2 domain containing protein tyrosine phosphatase-2 (SHP2) phosphatase activity in a subject in need thereof. The method comprises administering to the subject a specific oncogenic Src homology-2 domain containing protein tyrosine phosphatase-2 (SHP2) inhibitor having the formula (I):

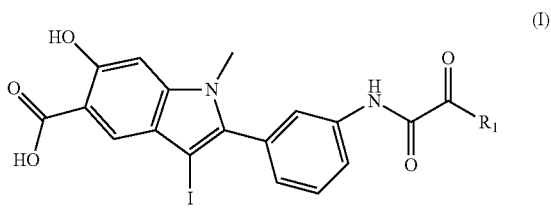

wherein $R_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

In another embodiment, the present disclosure is directed to a method for treating glomerulonephritis-associated diseases in a subject in need thereof. The method comprises administering to the subject a specific oncogenic Src homology-2 domain containing protein tyrosine phosphatase-2 (SHP2) inhibitor.

In yet another embodiment, the present disclosure is directed to a method for treating systemic lupus erythematosus (SLE) in a subject in need thereof. The method comprises administering to the subject a specific oncogenic Src homology-2 domain containing protein tyrosine phosphatase-2 (SHP2) inhibitor.

BRIEF DESCRIPTION OF THE DRAWINGS

FIG. 4A depicts the effect of SHP2 differential binding to a specific phospho-tyrosyl complex, whereby increased SHP2 activity and association with focal adhesion kinase (FAK) leads to its dephosphorylation and also to increased p85 phosphorylation (see also FIG. 8) in SLE-prone mice, as analyzed in Example 3.

FIG. 4B depicts the effect of preferential SHP2 binding to focal adhesion kinase (FAK) in SLE-prone mice, as analyzed in Example 3. Arrow at 85 kDa indicates hyperphosphorylated p85.

FIG. 5A depicts the protein domain structure of focal adhesion kinase (FAK).

FIG. 5B is a schematic illustrating activation of FAK upon phosphorylation and interaction with src leading to downstream ERK signaling.

FIGS. 14A-14F depict by histology (as assessed by H&E staining) the effect of SHP2 inhibition on kidney disease and its ability to reduce the crescentic glomerulonephritis in SLE-prone mice, as analyzed in Example 9.

FIGS. 15A-15F depict the effect of SHP2 inhibition on fibrosis (as assessed by Masson's trichrome staining) in SLE-prone mice, as analyzed in Example 9.

FIGS. 16A-16F depict the effect of SHP2 inhibition on immune cell infiltration and severity of glomerulonephritis/kidney disease (as assessed by Periodic acid-Schiff staining) in SLE-prone mice, as analyzed in Example 9.

FIGS. 18A-18D depict the effect of SHP2 inhibition on the size of germinal center in the spleen of SLE-prone mice, as analyzed in Example 11.

FIGS. 30A & 30B depict that SHP2 inhibition prevents proliferation and clonal expansion of cultured T cells isolated from peripheral blood mononuclear cells derived from normal or SLE-disease active human patients, as analyzed in Example 15.

DETAILED DESCRIPTION OF THE DISCLOSURE

Figure 1:
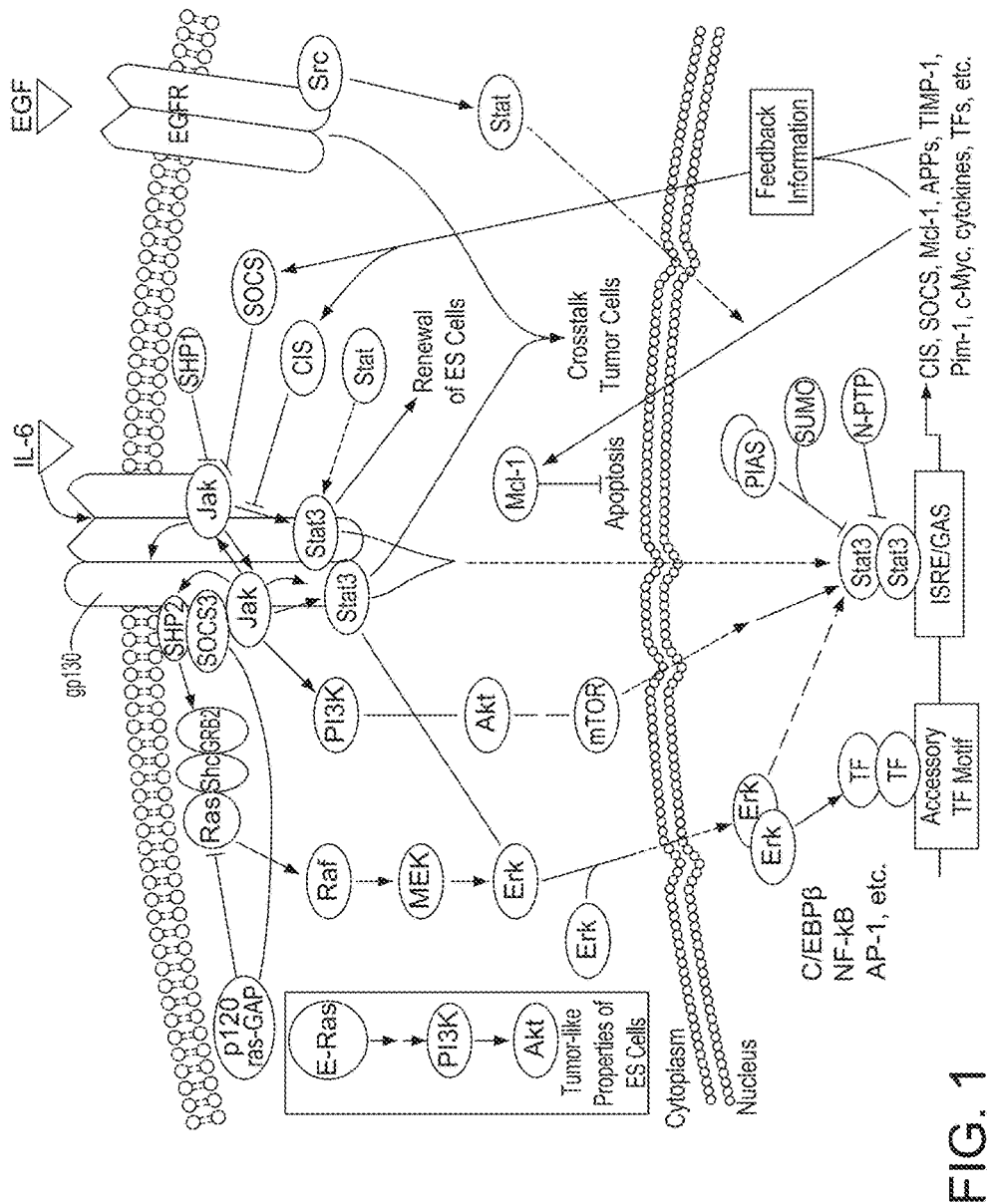
FIG. 1 depicts the general role of SHP2 in cytokine signaling.

The present disclosure is generally directed to methods of administering SHP2 inhibitors for treating glomerulonephritis-associated diseases. More particularly, hydroxyindole carboxylic acids of the general formula:

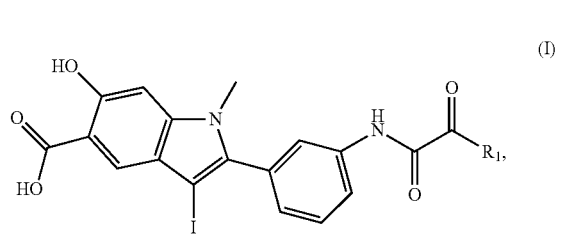

wherein $R_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur, have been synthesized and shown to inhibit SHP2. As further discussed in the Examples below, by inhibiting SHP2 activity, which has now been found to play a key role in the molecular pathogenesis of glomerulonephritis-associated diseases such as SLE, a novel therapeutic approach to treating patients for glomerulonephritis-associated disease pathogenesis has been found.

Exemplary hydroxyindole carboxylic acids of formula (I) selectively inhibit protein tyrosine phosphatases such as SHP2 with $IC_{50}$ values as shown in Tables 1 and 2.

TABLE 1

$IC_{50}$ values (μM) of a hydroxyindole carboxylic acid formula (I) library (11a (L97)) series for SHP2.

| ID | $R_1$ | $IC_{50}$ (μM) |
|---|---|---|
| 10a (Core 97) | OH | 14.4 ± 1.8 |
| 11a-1 (L97M74) |  | 0.20 ± 0.02 |

TABLE 1-continued $IC_{50}$ values (μM) of a hydroxyindole carboxylic acid formula (I) library (11a (L97)) series for SHP2.

| ID | $R_1$ | $IC_{50}$ (μM) |
|---|---|---|
| 11a-2 (L97N08) |  | 0.62 ± 0.05 |
| 11a-3 (L97M50) |  | 0.66 ± 0.03 |
| 11a-4 (L97M61) |  | 0.76 ± 0.11 |
| 11a-5 (L97M48) | | 0.77 ± 0.15 |
| 11a-6 (L97M52) | | 0.86 ± 0.14 |
| 11a-7 (L97M93) | | 1.05 ± 0.09 |
| 11a-8 (L97M24) | | 1.2 ± 0.21 |
| 11a-9 (L97M77) | | 1.25 ± 0.06 |
| 11a-10 (L97N15) | | 1.35 ± 0.31 |

TABLE 1-continued

IC$_{50}$ values (μM) of a hydroxyindole carboxylic acid formula (I) library (11a (L97)) series for SHP2.

| ID | R$_1$ | IC$_{50}$ (μM) |
|---|---|---|
| 11a-11 (L97M21) | HN—(3-Cl-phenyl) | 1.46 ± 0.45 |
| 11a-12 (L97M63) | HN—(4-imidazol-1-yl-phenyl) | 1.49 ± 0.15 |
| 11a-13 (L97M30) | HN—(4-Cl-3-CF$_3$-phenyl) | 1.76 ± 0.08 |
| 11a-14 (L97M73) | HN—(5-phenyl-1,3,4-thiadiazol-2-yl) | 1.79 ± 0.15 |
| 11a-15 (L97N95) | HN—(4-F-phenyl) | 1.84 ± 0.09 |
| 11a-16 (L97N13) | HN—(thiazol-2-yl) | 2.31 ± 0.28 |
| 11a-17 (L97M32) | HN—(3-OCF$_3$-phenyl) | 2.39 ± 0.15 |
| 11a-18 (L97M18) | HN—(3-Br-phenyl) | 2.73 ± 0.55 |
| 11a-19 (L97N07) | HN—(3-F-phenyl) | 4.66 ± 0.5 |

TABLE 1-continued

IC$_{50}$ values (μM) of a hydroxyindole carboxylic acid formula (I) library (11a (L97)) series for SHP2.

| ID | R$_1$ | IC$_{50}$ (μM) |
|---|---|---|
| 11a-20 (L97M23) | HN—(3-I-phenyl) | 5.42 ± 1.01 |

TABLE 2

IC$_{50}$ values (μM) of 11a-21 to 11a-26 (L97L02-08) series for SHP2.

| ID | R | IC$_{50}$ (μM) |
|---|---|---|
| 11a-1 L97M74 | HN—(4-(thiophen-3-yl)phenyl) | 0.20 ± 0.02 |
| 11a-21 L97L08 | HN—(4'-CN-biphenyl-4-yl) | 0.22 ± 0.01 |
| 11a-22 L97L07 | HN—(3'-CN-biphenyl-4-yl) | 0.31 ± 0.02 |
| 11a-23 L97L03 | HN—(2-(5-(hydroxymethyl)furan-2-yl)phenyl) | 0.37 ± 0.01 |
| 111a-24 L97L05 | HN—(3-(furan-2-yl)phenyl) | 0.38 ± 0.01 |

TABLE 2-continued

IC$_{50}$ values (μM) of 11a-21 to 11a-26 (L97L02-08) series for SHP2.

| ID | R | IC$_{50}$ (μM) |
|---|---|---|
| 11a-25 L97L06 | | 0.42 ± 0.02 |
| 11a-26 L97L02 | | 0.63 ± 0.04 |

In one particularly suitable embodiment, the hydroxyindole carboxylic acid for use in the methods of the present disclosure is L97M74, having the formula (II):

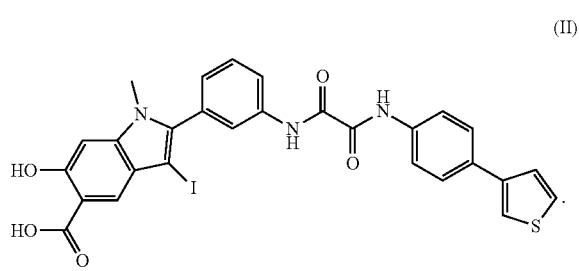 [SMILES: Cn1c(-c2cccc(NC(=O)C(=O)Nc3ccc(-c4ccsc4)cc3)c2)c(I)c2cc(C(=O)O)c(O)cc21]

(II)

The hydroxyindole carboxylic acids used in the methods of the present disclosure have been found to specifically inhibit protein tyrosine phosphatases, and particularly, SHP2, with an IC$_{50}$ of from about 0.2 μM to about 100 μM, including from about 2 μM to about 56 μM, including from about 4.5 μM to about 20 μM, and also including from about 0.2 μM to about 16 μM, and from about 2 μM to about 10 μM. In particularly suitable embodiments, the hydroxyindole carboxylic acids have been found to specifically inhibit protein tyrosine phosphatases with an IC$_{50}$ of less than 1 μM, including from about 0.2 μM to less than 1 μM, including from about 0.2 μM to about 0.7 μM, including from about 0.2 μM to about 0.5 μM, and including about 0.25 μM. The hydroxyindole carboxylic acid of formula (II) (L97M74) has an IC$_{50}$ value for SHP2 of 0.20 μM+0.02.

The general synthesis methods for preparing the hydroxyindole carboxylic acids of formulas (I) and (II) are described in PCT/US2014/035435, entitled Hydroxyindole Carboxylic Acid Based Inhibitors for Oncogenic SRC Homology-2 Domain Containing Protein Tyrosine Phosphatase-2 (SHP2), filed Apr. 25, 2014, which is herein incorporated by reference to the extent it is consistent herewith.

The SHP2 inhibitor can be administered to a subject in need thereof to inhibit SHP2 activation, thereby increasing FAK phosphorylation, increasing ERK signaling, and decreasing AKT signaling (see FIG. 1 for cytokine signaling overview). It has been found that such regulation of these pathways can provide a treatment for the progression of glomerulonephritis-associated diseases, and in particular, the progression of pathogenesis of postinfectious rapidly progressive glomerulonephritis (RPGN), idiopathic RPGN, SLE, Goodpasture's syndrome, vasculitis (e.g., polyuarteritis nodosa), Wegener's granulomatosis, Henoch-Schonlein purpura, essential cryoglobulinemia, acute proliferative glomerulonephritis, microscopic polyangiitis, Churg-Stauss Syndrome, IgA neuropathy, and the like, and further, can reduce/prevent/eliminate the conditions resulting from these diseases. In one particularly suitable embodiment, it has been found that inhibition of SHP2 activation can reduce/prevent/eliminate the conditions resulting from SLE. As used herein, "subject in need thereof" refers to a subset of subjects in need of treatment/protection from SLE. Some subjects that are in specific need of treatment may include subjects who are susceptible to, or at elevated risk of, experiencing SLE and symptoms of SLE. Subjects may be susceptible to, or at elevated risk of, experiencing symptoms of SLE due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

Typically, the SHP2 inhibitor is administered in an amount such to provide a therapeutically effective amount of the inhibitor to the subject. The term "therapeutically effective amount" as used herein, refers to that amount of active compound (i.e., SHP2 inhibitor) or pharmaceutical agent that elicits the biological or medicinal response in a tissue system, animal or human that is being sought by a researcher, veterinarian, medical doctor or other clinician, which includes alleviation of the symptoms of the condition, disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the inhibitor described herein may be decided by the attending physician within the scope of sound medical judgment. The specific therapeutically-effective dose level for any particular subject will depend upon a variety of factors, including the condition, disease or disorder being treated and the severity of the condition, disease or disorder; activity of the specific inhibitor employed; the specific system employed; the age, body weight, general health, gender and diet of the subject: the time of administration, route of administration, and rate of excretion of the specific inhibitor employed; the duration of the treatment; drugs used in combination or coincidentally with the specific inhibitor employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of the inhibitor described herein. Further, it is appreciated that the co-therapies described herein may allow for the administration of lower doses of inhibitor that show such toxicity, or other undesirable side effect, where those lower doses are below thresholds of toxicity or lower in the therapeutic window than would otherwise be administered in the absence of a co-therapy.

In particularly suitable embodiments, the SHP2 inhibitor is administered to the subject in amounts ranging from about 1 mg/Kg body weight/day to about 25 mg/Kg body weight/day, including from about 2.5 mg/Kg body weight/day to about 15 mg/Kg body weight/day, including from about 5.0 mg/Kg body weight/day to about 10 mg/Kg body weight/day, and including about 7.5 mg/Kg body weight/day.

The term "administering" as used herein includes all means of introducing the SHP2 inhibitor described herein to the subject, including, but are not limited to, oral (po), intravenous (iv), intramuscular (im), subcutaneous (sc), parenteral, transdermal, inhalation, buccal, ocular, sublingual, vaginal, rectal, and the like. The inhibitor described herein may be administered in unit dosage forms and/or formulations containing conventional nontoxic pharmaceutically-acceptable carriers, adjuvants, and vehicles.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustratively, administering includes local use, such as when administered locally to the site of disease, injury, or defect, or to a particular organ or tissue system. Illustrative local administration may be performed during open surgery, or other procedures when the site of disease, injury, or defect is accessible. Alternatively, local administration may be performed using parenteral delivery where the inhibitor described herein is deposited locally to the site without general distribution to multiple other non-target sites in the subject being treated. It is further appreciated that local administration may be directly in the injury site, or locally in the surrounding tissue. Similar variations regarding local delivery to particular tissue types, such as organs, and the like, are also described herein.

In some embodiments, a therapeutically effective amount of SHP2 inhibitor in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the inhibitor can be administered in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The SHP2 inhibitor-containing formulations may contain anywhere from about 0.1% to about 99.9% active ingredients, depending upon the selected dose and dosage form.

The following examples further illustrate specific embodiments of the present disclosure; however, the following illustrative examples should not be interpreted in any way to limit the disclosure.

EXAMPLES

Materials and Methods

Human Peripheral Blood Mononuclear Cell Isolation

All SLE human cells in the following Examples were isolated from SLE patients diagnosed according to the American College of Rheumatology classification criteria and recruited from the Division of Rheumatology at Beth Israel Deaconess Medical Center, Boston, Mass., under IRB protocol 2006-P-0298. Healthy gender- and age-matched control cells were also used for the Examples herein. Briefly, peripheral venous blood was collected in heparin-lithium tubes and peripheral blood mononuclear cells were prepared with ficoll-Paque centrifugation, as previously described in Grammatikos et al., *Clin Immunol.* 2014; 150: 192-200.

Mice

All mice utilized herein were maintained in a specific pathogen free (SPF) animal facility at Beth Israel Deaconess Medical Center (BIDMC). All procedures were performed in accordance with the NIH Guide for the Care and Use of Laboratory Animals and approved by the Institutional Animal Care and Use Committee (IACUC) at BIDMC.

Briefly, female MRL/MpJ-fas lpr (MRL/lpr), MRL/Mpj and C57BL/6J mice were purchased from the Jackson Laboratory (Bar Harbor, Me.). For experiments, mice within each group were ip injected with either vehicle (DMSO) or the SHP2 inhibitor (7.5 mg/kg/per day). Testing continued for a period of 6 weeks, starting at 11 weeks of age to 17 weeks. Body weight was measured daily and treatment dosage was adjusted accordingly. At the end of the treatment period, mice were sacrificed with $CO_2$ exsanguination and SLE targeted organs were removed. For each mouse, spleen, kidney, and heart weight were calculated. In addition, total animal body weight and tibia length were measured. Peripheral blood/serum was also collected for use in the cytokine assays described below.

Longevity Study

Female MRL/lpr mice were used for a survival/longevity curve analysis. Mice either ip injected with vehicle (DMSO) or SHP2 inhibitor (7.5 mg/kg/each day) were followed beginning at 11 weeks of age to assess tolerance to the inhibitor and longevity/survival curve. The testing was terminated when the last mouse in the control group died, at 26 weeks.

Histology

Harvested organs (kidney, spleen, and heart) to be used to assess morphometry and histochemistry were flushed with PBS, perfusion fixed in Bouin's reagent, and paraffin embedded. Sections (5 µm) were stained with Hematoxylin and Eosin (H&E), Periodic acid-Schiff stain (PAS), Masson-Trichrome, or reticulin staining at the Harvard Medical School Rodent Histopathology Core and scored using an unbiased approach, in which histology scores of 1 (normal) to 5 (most severe pathology) were designated to tissue sections which were only numerically labeled and in no particular order (by Dr. Roderick Bronson, director of the Rodent Histopathology Core, Harvard Medical School). Numerical sections were later decoded, marked for their designated score, and statistically analyzed. Images of the tissue sections were obtained and quantified on a Keyence BZ-9000 Microscope (Keyence Corporation, Itasca, Ill.).

Urinalysis

To determine kidney function, urine was collected before mice were sacrificed. Albumin and creatinine in the urine were measured using colorimetric assays according to the manufacturer's instructions (Albuwell M; The creatinine companion, Exocell), as described below. The kidney function was calculated as ratio of albumin to creatinine levels.

Blood Cell Counts

50 µl of peripheral blood was collected from mice upon sacrifice and was mixed with 5 mM EDTA anticoagulant to be used for blood cell counts (Hemavet 850FS), to determine numbers of white blood cells (neutrophil, lymphocytes, monocytes, eosinophil and basophil), red blood cells and platelets. In addition, peripheral blood isolated from MRL/lpr mice either treated with vehicle (DMSO) or SHP2 inhibitor was used to count the percentage of lymphocyte subsets, including B cells, CD4+, CD8+ and double negative (DN) T cells through flow cytometry (see below).

Total Cell Isolation from Various SLE-Prone Tissues (Kidney, Lung, Spleen and Axillary Lymph Nodes)

Kidney, spleen, lung, and axillary lymph nodes were excised from either vehicle or drug-treated mice, and single cell suspensions were obtained by teasing the organs through a nylon mesh. Briefly, kidneys were cut into small pieces and homogenized on a 70 µm nylon mesh in 5 ml of Hank's Balanced Salt Solution (HBSS) buffer. All of the homogenized tissues and cells were transferred to new 50 ml tubes and digested with collagenase type 4 (100 ug/ml) (Worthington Biochemical Corp., Freehold, N.J.) in HBSS for 30 minutes to 2 hours (37° C.) on a rotating shaker. After digestion, the cells were centrifuged at 2000 rpm for 10 minutes, and the kidney cell isolates were generated, which included infiltrated immune cell subsets.

Isolation of cells from lung was similar to isolation of cells from kidney, with the exception of the need for digestion of the tissue with collagenase.

Spleens were cut into 2 to 3 pieces each and homogenized on a 70 µm nylon mesh in 5 ml of HBSS buffer. The cells were filtered through a 70 µm nylon mesh to a new 50 ml tube and centrifuged at 2000 rpm for 5 minutes at room temperature. The pellets were dissolved in 1-2 ml of red blood cell (RBC) lysis buffer (Sigma R7757) for 2-5 minutes to lyse the RBCs. 30 ml of 1×HBSS buffer was added and the homogenate was centrifuged at 2000 rpm for 10 minutes. The pellet, containing immune cell subsets and remaining tissue aggregates, was further dissolved in 5 ml of HBSS and additionally filtered through a new 70 µm nylon mesh to remove these aggregates. Finally the remaining cell suspension was centrifuged at 2000 rpm at 4° C. for 5 minutes to collect the splenocytes, which included the immune cell subsets.

Isolation of cells from axillary lymph nodes (double negative cells) was similar to isolation of cells from spleen, with the exception of the step that included lysis of RBCs.

All the isolated cell pellets were dissolved in 1 ml of 2% FBS/PBS buffer and in preparation for the flow cytometry assay (see below).

Flow Cytometry

To identify immune cell subsets, isolated cells from tissues were immunostained with mouse antibodies targeted against CD3ε (145-2C11, BioLegend, San Diego, Calif.), CD4 (GK1.5, BioLegend), CD8 (53-6.7, eBioscience, San Diego, Calif.), CD45 (30-F11, eBioscience), CD 19 (6125, BioLegend), CD11b (M1170, BioLegend), TCRαβ (H57-597, BioLegend), CD44 (IM7, BioLegend), B220 (RA3-6B2, B.D. PHARMINGEN, BD Biosciences, San Jose Calif.), CD138 (281-2, BioLegend), CD38 (CD28.2, BioLegend), Gr-1 (RB6.805, eBioscience), CD62L (DREG-56, BioLegend), and CD25 (PC61, BioLegend) for 30 minutes at 4° C. Samples were acquired on a LSR II flow cytometer (BD Biosciences) and the percentage of each sub-population of cells (B, T, monocytes, macrophage and neutrophils) was assessed by FlowJo [version 7.2.2 (Tree Star)]. Total cell numbers were counted using a hemocytometer. Absolute cell numbers for each sub-population were calculated based on the percentage of each population.

ELISA

ELISA assays were used to detect for the presence of various cytokines in mouse serum isolated from vehicle or drug-treated animals or from medium supernatant isolated from tissue cell cultures as described above. In addition, ELISA was also used to detect total IgG and dsDNA IgG from mouse serum and for the assay to detect urine albumin and creatinine levels. ELISA detection kits for mouse cytokines IL-6 and TNFα were purchased from eBioscience, mouse cytokines IL-17A, IFNγ, and human IFNγ were purchased from Biolegend, kits for the albumin and creatinine were purchased from Exocell, and kits for the serum IgG and anti-dsDNA IgG were purchased from Alpha Diagnostic (San Antonio, Tex.). ELISAs were all performed according to the manufacturer's instructions.

Cytokine analyses: In brief, capture antibodies for each cytokine were precoated on 96-well plates overnight at 4° C., then 100 µl of 5× diluted serum or 300× diluted supernatant medium was loaded on the precoated wells in duplicate and left overnight at 4° C. (with the exception of the human IFNγ assay isolated from supernatant medium, where the dilution used was 1:30). As per the protocol instructions, enzyme-antibody conjugate, TMB substrate and stopping buffer were added sequentially. The colorimetric analysis, as measured by optical density (OD) within each well, was determined using a microplate reader set at a wavelength of 450 nm. The cytokine concentrations were calculated and measured against a standard curve for each cytokine.

Serum IgG and anti-dsDNA IgG: 100 µl of 1:50000× diluted serum for IgG and 100 µl of 1:20000× diluted serum for dsDNA IgG were used and loaded onto a precoated 96-well plate in duplicate for 1 hour at room temperature. As per the protocol instructions, enzyme-antibody conjugate, TMB substrate and stopping buffer were added sequentially. The OD of the wells was determined using a microplate reader set at a wavelength of 450 nm.

Albumin and creatinine levels: For the albumin assay, collected mouse urine was diluted at 1:5200× and 50 µl was loaded onto an albumin precoated 96-well plate, followed by primary incubation, secondary incubation and colorimetric determination. For the creatinine assay, the urine was diluted 20× and loaded onto a 96-well plate, and picrate working solution and acid reagent were added sequentially according to protocol. Absorbance was assayed using a plate reader set at a wavelength of 495 nm.

Purification and Culture of Mouse and Human T Cells

Whole tissue cell cultures prepared from mouse spleen and axillary lymph nodes were generated as described above. From within this total cell preparation, total T cells from spleen and the double negative T cells from axillary lymph nodes were further purified through negative selection using a pan T cell isolation kit from Milenyi Biotec (San Diego, Calif.). In brief, 10 µl of pan T cell biotin-antibody cocktail, which includes monoclonal antibodies against CD11b, Cd11c, CD19, CD45R (B220), CD49b, CD105, anti MHC class II and ter-19, was added per $1 \times 10^7$ total cells, incubated on ice for 30 minutes, and then mixed with 30 µl of D-PBS/0.5% FBS (pH 7.2) per $1 \times 10^7$ cells. Next, 20 µl of anti-biotin beads were added per $1 \times 10^7$ cells and the reaction was kept on ice for another 30 minutes. After centrifuging at 2000 rpm for 5 minutes at 4° C., the pellet was resuspended in 2 ml of T cell isolation buffer (D-PBS, pH7.2, 0.5% FBS and 2 mM EDTA) and the T cells were purified through a magnetic sorting column (MACS).

Human T cells were purified from frozen peripheral blood mononuclear cells (PBMC) isolated from SLE or normal donor patients. Briefly, frozen PBMCs were thawed in a 37° C. water bath for 1 to 2 minutes, and then gently added to pre-warmed RPMI1640 medium with 10% FBS (total 10 ml). The cells were centrifuged at 2000 rpm for 5 minutes at room temperature. The cell pellet was washed with 5 ml of pre-warmed RPMI 1640 medium with 10% FBS three times, followed by a final D-PBS (no calcium, no magnesium buffer) wash. Human T cells were then purified by a Pan T Cell Isolation Kit (human) from Miltenyi Biotec, as described above.

The purity of isolated T cells routinely exceeded 94%. After purification, T cells were resuspended in RPMI1640 medium with 10% FBS and $1\times10^5$ cells/well in 100 ul total volume was loaded onto a 96-well plate, either left uncoated or precoated with anti-CD3 antibody (1 ug/ml) (OKT3; Biolegend). All cells loaded onto wells precoated with anti-CD3 antibody were also mixed with anti-CD28 antibody (0.5 µg/ml) (CD28.2; BioLegend) to help potentiate the T cell signaling response. Plated cells were cultured for 48 hours in either the presence of vehicle (DMSO) or Shp2 inhibitor (10 µg/ml). Following the incubation, 15 µl of medium was collected for various cytokine activity analyses.

T Cell Proliferation and Viability Assays

For cell viability, an MTT (thiazolyl Blue tetrazolium Bromide, M2128, Sigma, St. Louis, Mo.) assay was employed. Briefly, 10 µl of the MTT labeling reagent (final concentration 0.5 mg/ml) was loaded into each cell culture well (96-well plate) and then incubated for 4 hours in a humidified chamber. Following incubation, 100 µl of solublization solution (0.04N in absolute isopropanol) was added to each well, resuspended, and then incubated at 37° C. for an additional hour. Spectrophotometric absorbance of the samples was assessed using a microplate reader at a wavelength of 595 nm. T cell numbers/proliferation was assessed by cell count using a hemocytometer. In brief, $1\times10^5$ cells were plated in wells and cultured for 48 hours. 10 µl of cell suspension was then removed and mixed together with 10 µl of trypan blue solution (0.4%, T8154, Sigma). After mixing, 10 µl of the mixture was loaded onto the hemocytometer and the total average number of cells/well was calculated.

Echocardiography

Transthoracic echocardiography was conducted on non-anesthetized animals as described previously in Marin et al., *J Clin Invest*. 2011; 121:1026-1043, with a 13-MHz probe (Vivid 7, GE Medical Systems, Boston, Mass.) or Visual-Sonics Vevo 770 high-frequency ultrasound rodent imaging system (VisualSonics, Toronto, Ontario). GE Medical Systems or VisualSonics Vevo 770 software was used for data acquisition and subsequent analysis. Hearts were imaged in the 2-dimensional parasternal short-axis view, and an M-mode echocardiogram of the midventricular region was recorded at the level of the papillary muscles. Calculations of cardiac anatomic and functional parameters were carried out as described in Marin et al., *J Clin Invest*. 2011; 121:1026-1043.

Biochemical Analyses

Tissues (spleen, kidney, heart) isolated from either vehicle (DMSO) treated or SHP2 inhibitor treated WT C57/B16, MRL/MpJ, or MRL/lpr female mice were dissected, perfused in PBS, and immediately frozen in liquid $N_2$. Whole-cell lysates were prepared by homogenizing the tissue in radioimmunoprecipitation (RIPA) buffer (25 mmol/l Tris-HCl [pH 7.4], 150 mmol/l NaCl, 0.1% SDS, 1% NP-40, 0.5% sodium deoxycholate, 5 mmol/l EDTA, 1 mmol/l NaF, 1 mmol/l sodium orthovanadate, and a protease cocktail) at 4° C., followed by clarification at 14,000 g. Proteins were resolved by SDS-PAGE and transferred to PVDF membranes Immunoprecipitations were performed with anti-FAK (sc-558) or anti-SHP2 (sc-280) antibodies (Cell Signaling Technology) Immunoblots were performed on immunoprecipitated lysates or whole cell lysates, following the manufacturer's directions, with anti-Akt (sc-8312), anti-SHP2 (sc-280), anti-phospho 576-FAK (sc-16563-R), anti-FAK (sc-558) (Santa Cruz Biotechnology Inc., Dallas, Tex.); or anti-phospho-Akt (4060S), anti-phospho-Erk1/2 (9101L), anti-Erk1/2 (9102L), anti-p85 (4257S), anti-phospho-p70S6K (9234S), anti-p70S6K (9292L), anti-phospho-S6rp (2211S), and anti-S6rp (2217S) antibodies (Cell Signaling Technology, Danvers, Mass.); or anti-phospho-tyrosine (4G10) (Millipore, Billerica, Mass.). Bands were visualized with enhanced chemiluminescence and quantified by densitometry (developed by Wayne Rasband; ImageJ 1.41 software, http://rsbweb.nih.gov/ij/).

Immune Complex PTP Assays

PTP assays were conducted as previously described in Kontaridis et al., *J Biol Chem*. 2006; 281:6785-6792, using para-nitrophenyl phosphate (pNPP, obtained from Sigma) as substrate. Briefly, WT C57/B16, MRL/MpJ, or MRL/lpr tissue (spleen, kidney, heart) lysates were homogenized and lysed in RIPA buffer (but without sodium orthovanadate), and SHP2 was immunoprecipitated by using anti-SHP2 polyclonal antibodies (Santa Cruz Biotechnology Inc.) coupled to protein A-Sepharose Immune complexes were washed 3 times in RIPA buffer without sodium orthovanadate and once in wash buffer [30 mM HEPES (pH 7.4), 120 mM NaCl without pNPP]. For each sample, PTP assays were performed in triplicate at 37° C. in 50 µl of assay buffer [30 mM Hepes (pH 7.4), 120 mM NaCl, 5 mM dithiothreitol, 10 mM pNPP] containing 50 µl of the SHP2 beads. Reactions were terminated with 0.2 N NaOH and phosphate release was determined by measuring A410. Following the assays, immune complexes were recovered by centrifugation, boiled in 2×SDS-PAGE sample buffer, resolved by SDS-PAGE, and immunoblotted with polyclonal SHP2 antibodies (Santa Cruz Biotechnology Inc.) to ensure that equal amounts of SHP2 had been tested for phosphatase activity.

Statistics

All data are expressed as mean±SEM. Statistical significance was determined using 2-tailed Student's t test and 1-way ANOVA or 2-way repeated measure ANOVA, as appropriate. If ANOVA was significant, individual differences were evaluated using the Bonferroni post-test. For all studies, values of $p<0.05$ were considered statistically significant.

Example 1

In this Example, the potential for a mechanistic role for SHP2 in the pathogenesis of SLE was evaluated.

Particularly, tissue lysates from kidney, spleen, and heart from 5 female mice each of 8- and 16-week old WT, MRL/MpJ (lupus strain-control) and MLR/lpr mice were obtained Immune-complex phosphatase assays were performed to assess activity of SHP2 in SLE lysates.

Results

SHP2 Phosphatase Activity is Increased in SLE-Prone MRL/lpr Mice.

Figure 2:
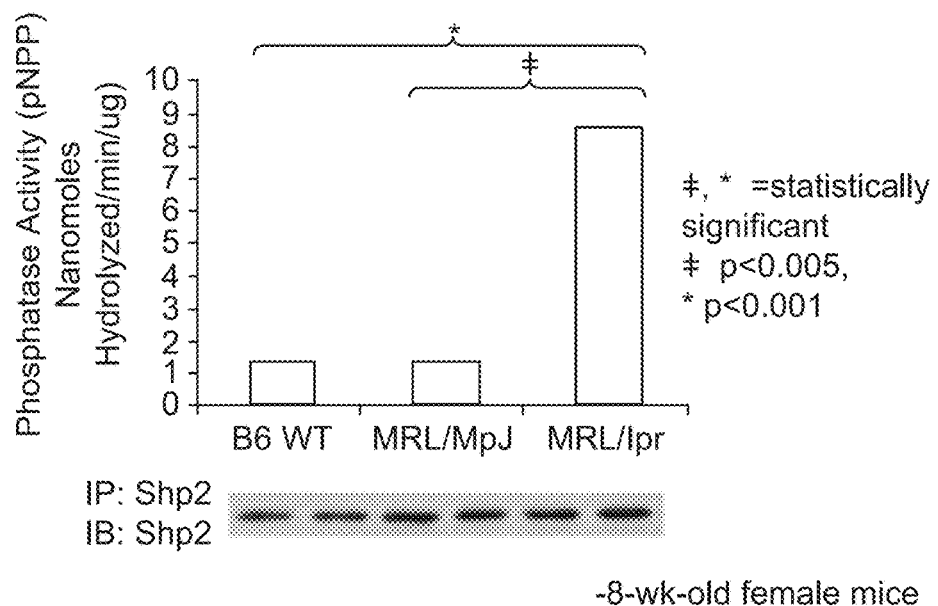
FIG. 2 depicts the increase in SHP2 phosphatase activity in SLE-prone mouse tissue lysates, as compared to control lysates, as analyzed in Example 1.

Unexpectedly, it was found that phosphatase activity was significantly increased (8-fold) in both 8-week (FIG. 2) and 16-week (data not shown) old MLR/lpr mice, as compared to both WT and MRL/MpJ control mice, showing SHP2 activity is upregulated in SLE.

Example 2

In this Example, SHP2 activity in peripheral blood mononuclear cells (PBMCs) from human SLE patients was evaluated and compared to activity in healthy human patients.

To determine whether elevated SHP2 activity was clinically relevant, SHP2 activity was measured in human PBMCs isolated from either normal female donors or SLE-disease active female patients (n=5 each).

Results

SHP2 activity is significantly increased in PBMC from SLE patients.

Figure 3:
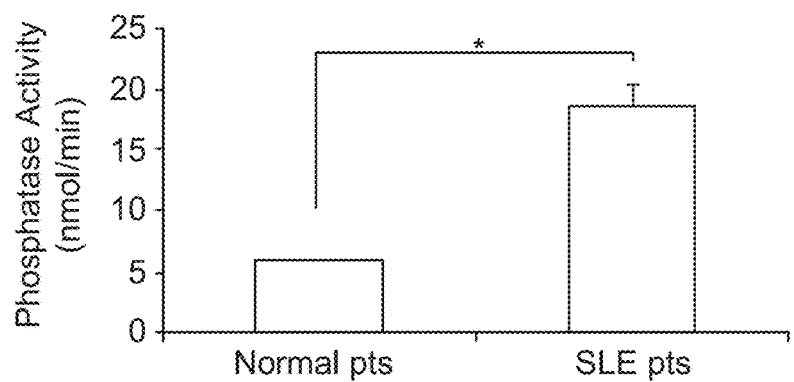
FIG. 3 depicts the increase in SHP2 phosphatase activity in peripheral blood mononuclear cells isolated from either normal or SLE disease active human subjects, as analyzed in Example 2.

As shown in FIG. 3, SHP2 activity was significantly increased in PBMCs from SLE patients, as compared to normal, further suggesting SHP2 activity is important in SLE disease. These results are consistent with the data from Example 1, and further demonstrate that SHP2 activity is upregulated in human patients with SLE.

Example 3

In this Example, the role of SHP2 in the signaling mechanism involved in SLE was evaluated.

SHP2 was immunoprecipitated from tissue lysates (kidney, spleen, and heart) obtained from 8-week old female WT and MLR/lpr mice and immunoblotted with phospho-tyrosyl antibodies.

Results

Distinct Tyrosyl-Phosphorylated Proteins Form a Complex with SHP2 in Tissue Lysates Isolated from SLE-Prone Mice.

Two tyrosyl-phosphorylated proteins were co-immunoprecitated with SHP2 in each of the tissues, as compared to WT controls (FIGS. 4A & 4B). A proteomics screen was further conducted to identify these proteins by mass spectrometry.

The p120 kDa dephosphorylated protein in SLE lysates was identified as Focal Adhesion Kinase (FAK), a likely substrate target for SHP2 in SLE, and a p85 kDa hyper-tyrosyl phosphorylated protein was identified as the p85 subunit of PI3K, a critical upstream regulator of the AKT/mTOR signaling pathway (FIG. 4B).

Example 4

In this Example, the interaction of SHP2 and FAK was evaluated. FAK is a cytoplasmic tyrosine kinase that plays a major role in cytokine signaling, although its role in SLE has, before now, remained unclear. Significantly, SHP2 is a regulator of FAK, and both ERK and AKT signaling can be directly regulated by FAK.

To assess whether SHP2 plays a role in FAK regulation, the association of SHP2 with FAK at its critical regulatory site, Y397, was assessed. SHP2 was immunoprecipitated from tissue lysates obtained from the MRL/lpr mice.

Results

SHP2 Directly Binds to FAK at its Critical Y397 Regulatory Site in SLE and Mediates Direct Dephosphorylation of the Downstream Erk Activation Sites on FAK (FIG. 4B).

Figure 6:
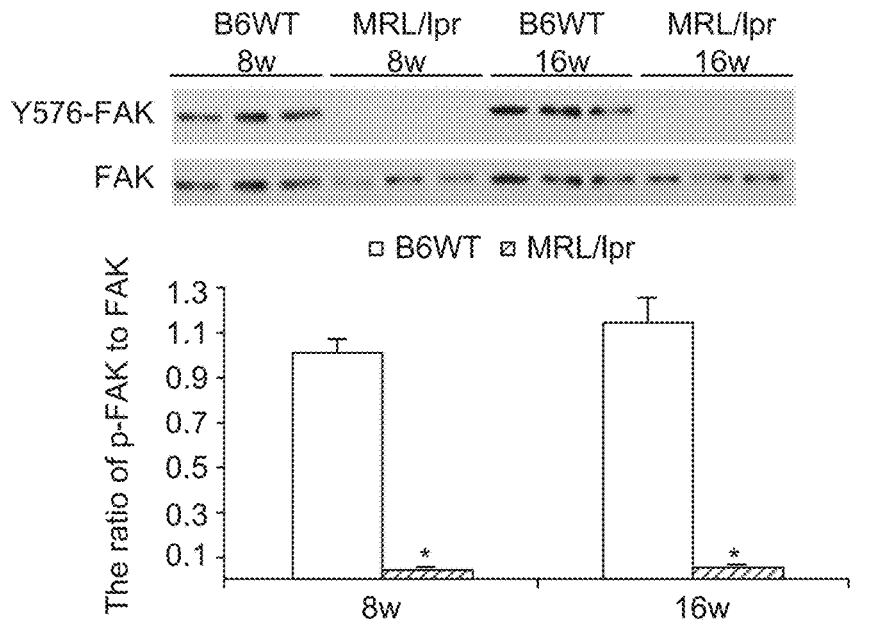
FIG. 6 depicts the decrease in focal adhesion kinase (FAK) phosphorylation in SLE-prone tissue lysates, as compared to control lysates, as analyzed in Example 4.

SHP2 was shown to preferentially form a complex with FAK in SLE-prone tissue lysates (FIG. 4B), suggesting that FAK is a specifically-targeted SHP2 substrate and is dephosphorylated in SLE-prone mice. FIGS. 5A and 5B depict schematics illustrating the activation of FAK upon phosphorylation and interaction with src leading to downstream ERK signaling. As shown in FIG. 6, increased activation and association with SHP2 led to dephosphorylation of FAK on downstream ERK activation sites.

Example 5

In this Example, the effects of increased SHP2 activity on ERK activation in SLE were evaluated.

ERK1/2 phosphorylation in tissue (kidney, spleen, and heart) lysates isolated from 8- and 16-week old WT and MLR/lpr mice was analyzed.

Results

ERK Phosphorylation is Decreased in MRL/lpr Lysates.

Figure 7:
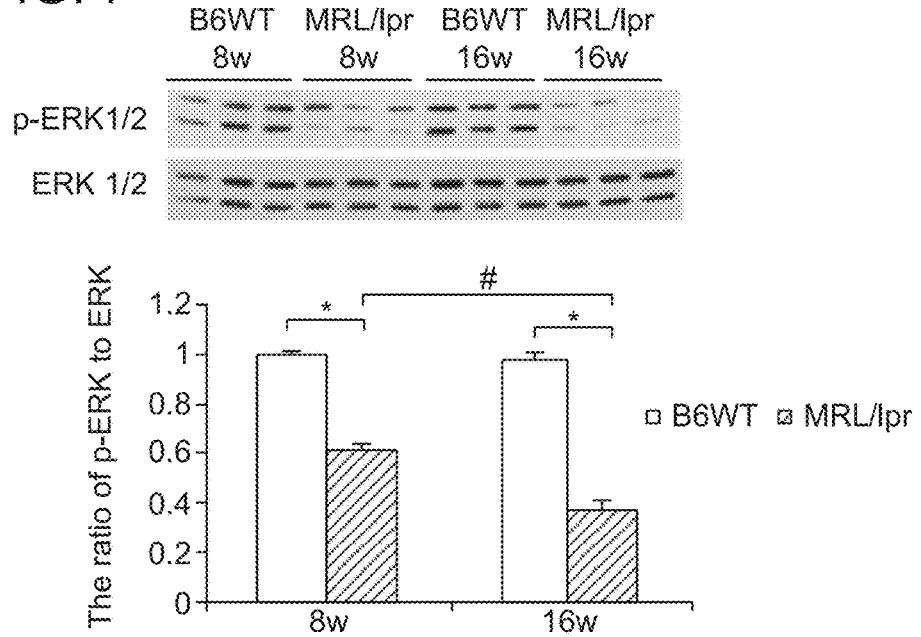
FIG. 7 depicts the decrease in extracellular signal-regulated kinases (ERK) signaling in SLE-prone tissue lysates, as compared to control lysates, as analyzed in Example 5.

As shown in FIG. 7, ERK activity was decreased in MRL/lpr lysates, as compared to WT. FAK dephosphorylation by SHP2 on its ERK activation sites likely leads to the decreased ERK activity observed in these SLE tissue lysates. Moreover, decreased ERK activity in SLE may mediate DNA hypo-methylation, which can lead to hyperactivation of autoreactive and inflammatory T and B cells.

Example 6

In this Example, the interaction of SHP2 complexed with FAK and the p85 subunit of PI3K was evaluated.

In addition to its actions on ERK signaling, FAK can also recruit and bind the p85 subunit of PI3K to positively drive downstream AKT signaling. Tissue (kidney, spleen, and heart) lysates were isolated from 8- and 16-week old WT and MLR/lpr mice and assessed.

Results

SHP2 Binding to FAK Recruits Tyrosyl-Phosphorylated p85 Subunit of PI3K.

Figure 8A:
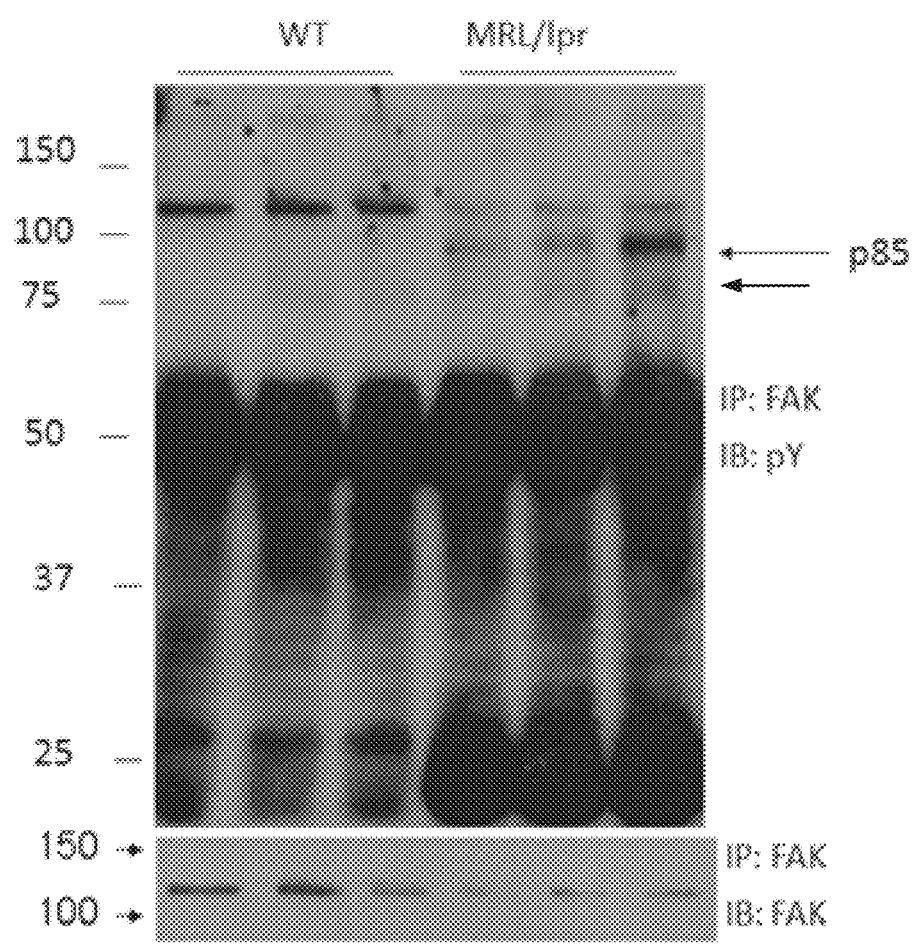
FIG. 8A depicts the effect of FAK differentially binding to a specific phospho-tyrosyl complex, which includes p85 and SHP2, whereby there is decreased FAK phosphorylation, but an increased association with phosphorylated SHP2 and p85 proteins in SLE-prone mice, as analyzed in Example 6.
Figure 8B:
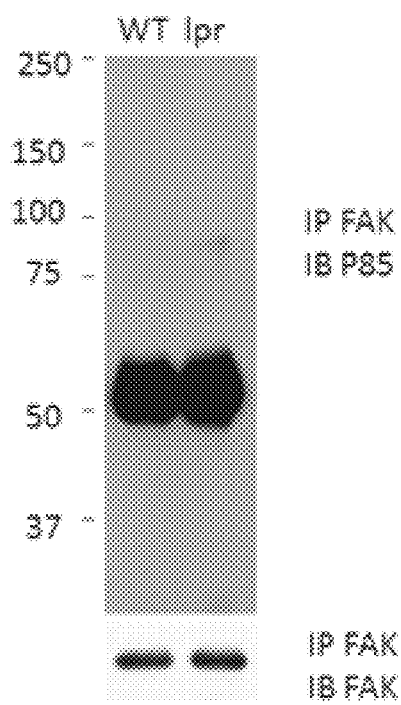
FIG. 8B depicts the preferential binding of FAK to the p85 subunit of PI3K in SLE-prone mice, as analyzed in Example 6.
Figure 8C:
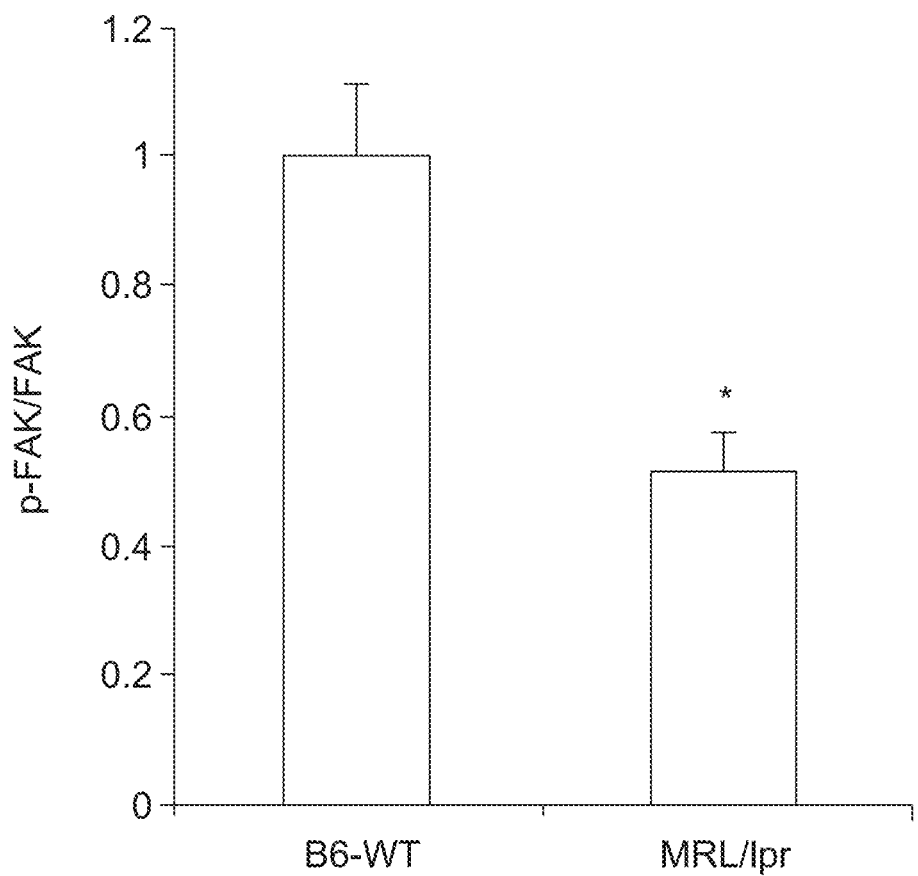
FIG. 8C depict the quantified decrease in FAK phosphorylation in SLE-prone mice, as analyzed in Example 6.

In SLE tissue lysates, p85 was preferentially recruited to FAK. Particularly, hyperphosphorylated p85 was recruited to FAK through increased association with SHP2 in SLE (FIGS. 8A & 8B). FAK specifically binds to SHP2 and to the p85 subunit of PI3K in SLE. As seen in FIG. 8A, the SHP2 dephosphorylated band at 125 kDa is FAK and the band at 85 kDa is p85. The band at ~70 kDa is SHP2. Quantification for the decrease in FAK phosphorylation in SLE is shown in FIG. 8C.

Example 7

In this Example, the effects of increased SHP2 activity on AKT signaling in SLE were evaluated.

Tissue (kidney, spleen, and heart) lysates were isolated from 8- and 16-week old WT and MLR/lpr mice.

Results

AKT Pathway is Elevated in SLE Lysates.

Figure 9:
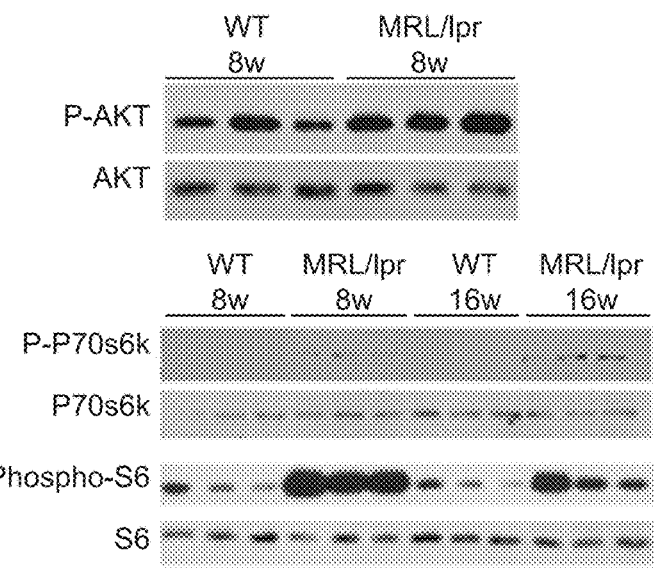
FIG. 9 depicts the increase in AKT activation, as well as its downstream effectors, p70S6K and ribosomal S6 kinase activities, in SLE-prone tissue lysates, as compared to control, as analyzed in Example 7.

As shown in FIG. 9, consistent with inflammatory responses which activate AKT, MRL/lpr tissue lysates showed increased AKT signaling, and downstream S6K activity, in both 8- and 16-week-old MRL/lpr mice. Increased AKT signaling may contribute to the increased accumulation of immune complexes observed in SLE.

Taken with the results from Examples 5 and 6, these data suggest a mechanism by which SHP2, through regulation of FAK phosphorylation, is required to suppress ERK activation and activate AKT signaling in SLE, a possible integral mechanism in SLE pathogenesis.

Example 8

In this Example, the effect of an inhibitor of SHP2 activity on inhibiting SLE disease progression was evaluated.

To determine whether normalization of SHP2 activity could inhibit SLE disease progression, WT B6, MRL/MpJ, MRL/lpr and MRL/lpr mice were treated with either vehicle or the SHP2 inhibitor, L97M74, (7.5 mg/kg) daily for 4 weeks beginning at 12 weeks of age. Tissue (kidney, spleen, heart, and thymus) was collected from the mice at the end of the study, at 16 weeks of age.

Results

SHP2 Inhibitor Normalizes SHP2 Activity and Reverses Aberrant ERK and AKT Signaling.

Figure 10A:
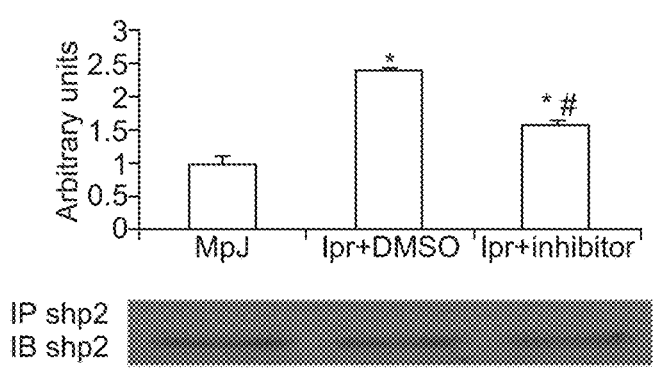
FIGS. 10A & 10B depict the ability of the SHP2 inhibitor to normalize SHP2 activity at the 7.5 mg/kg/day dose in SLE-prone tissue lysates, and the effects of SHP2 inhibition on reversing p-ERK, p-AKT, and p-ribosomal protein S6 kinase signaling defects, as analyzed in Example 8.
Figure 10B:
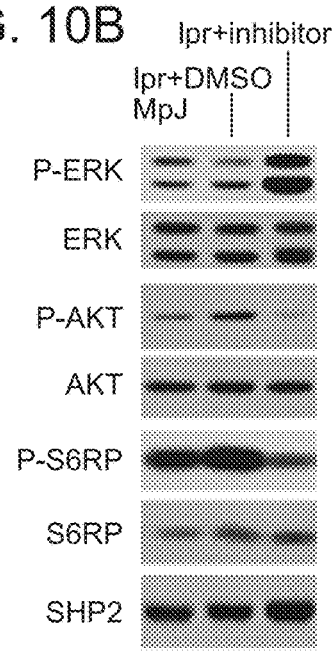

Remarkably, as shown in FIGS. 10A-10B, the lysates isolated from SHP2 inhibitor-treated MRL/lpr mice not only normalized SHP2 activity back to levels of WT, but also reversed aberrant downstream ERK and AKT signaling.

Example 9

In this Example, the effect of L97M74 on SHP2 activity on inhibiting SLE disease progression in mice was evaluated.

To determine whether inhibition of SHP2 activity affected SLE disease progression, each of the SLE target tissues (i.e., skin, kidney, spleen) was tested in both treated and untreated SLE-prone mice. Particularly, tissues were tested as: WT treated with inhibitor, WT treated with DMSO (vehicle), MRL/mpJ treated with inhibitor, MRL/mpJ treated with DMSO (vehicle), MRL/lpr treated with inhibitor, and MRL/lpr treated with DMSO (vehicle).

Figure 11A:
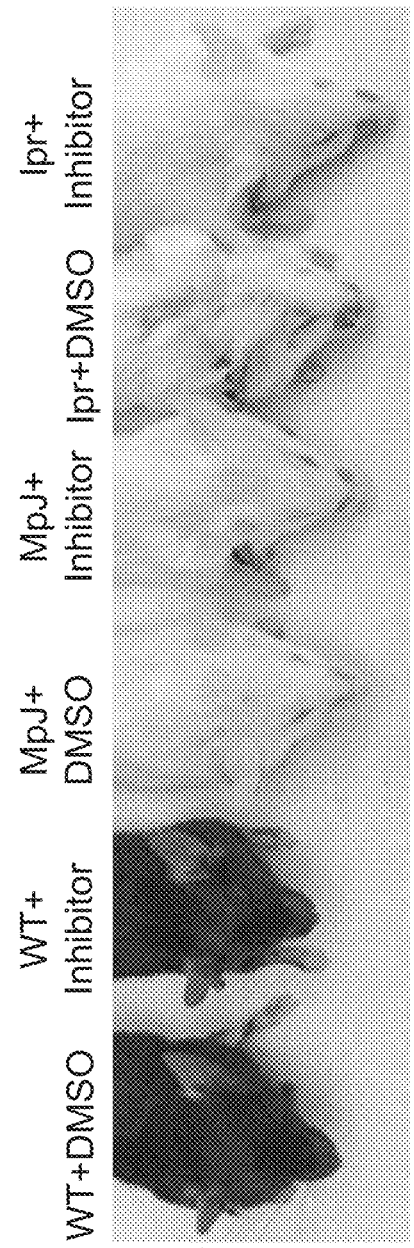
FIG. 11A depicts the effect of SHP2 inhibition on protecting subjects against skin lesions, as analyzed in Example 9.
Figure 11B:
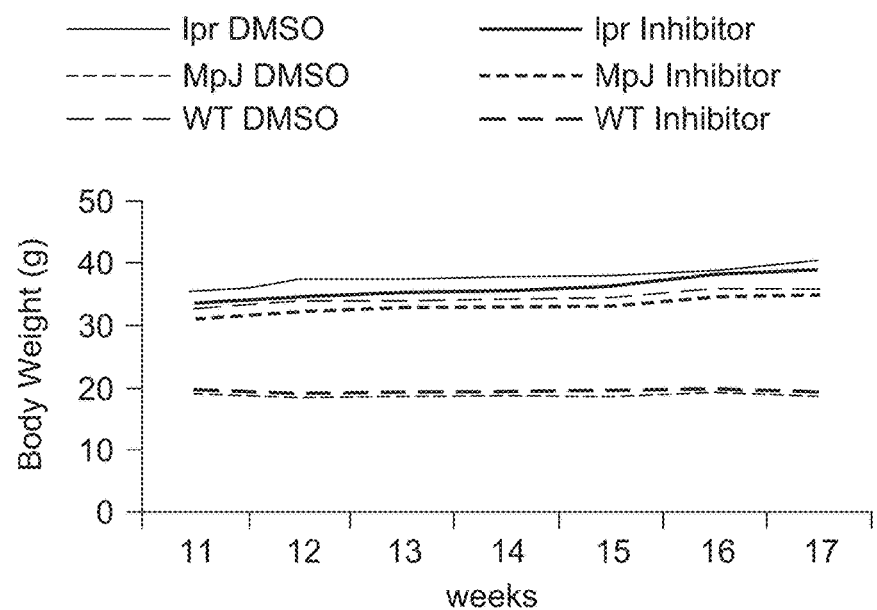
FIGS. 11B & 11C depict 1) no/minimal cytotoxic effects of SHP2 inhibition on mice as assessed by no change in body weight during treatment period and 2) an increased longevity/survival effect on SLE mice with treatment of SHP2 inhibitor, as assessed by Kaplan-Meier survival curve, as analyzed in Example 9.
Figure 11C:
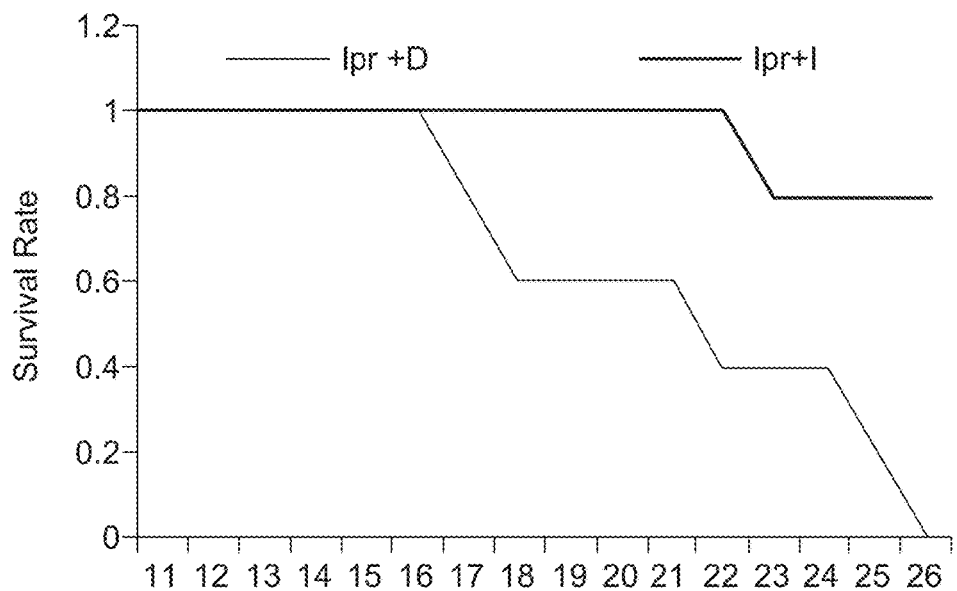

At a dose of 7.5 mg/kg/day, the SHP2 inhibitor reduced the skin lesions/inflammation (FIG. 11A), had no obvious cytotoxic effects during the treatment period (FIG. 11B) and significantly increased lifespan of SLE-prone mice (FIG. 11C).

Figure 12A:
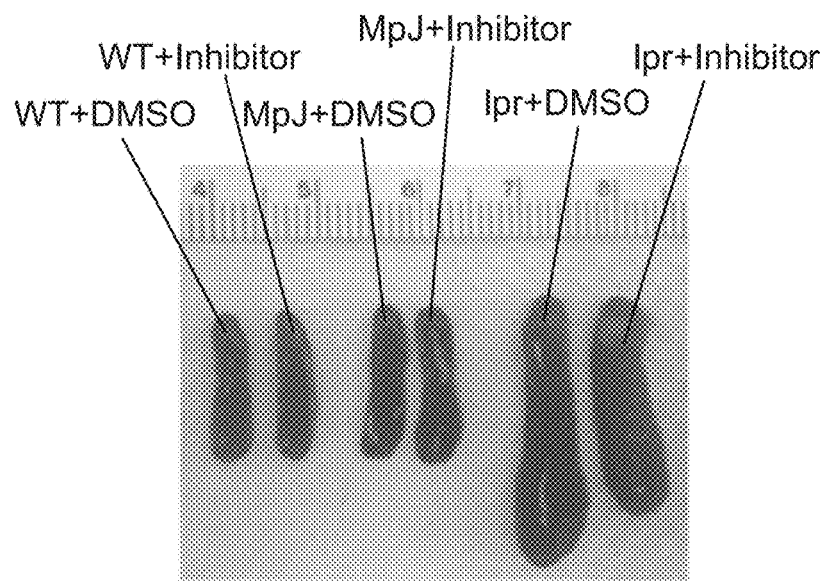
FIGS. 12A & 12B depict the effect of SHP2 inhibition on reducing spleen size and weight in SLE-prone mice, as analyzed in Example 9.
Figure 12B:
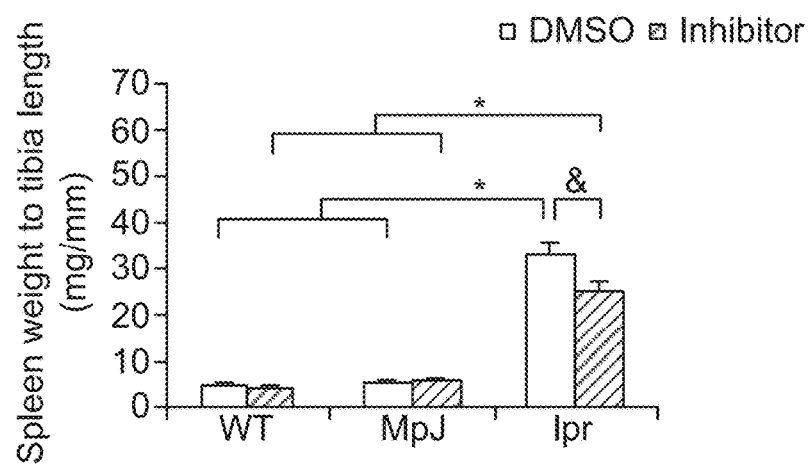
Figure 13A:
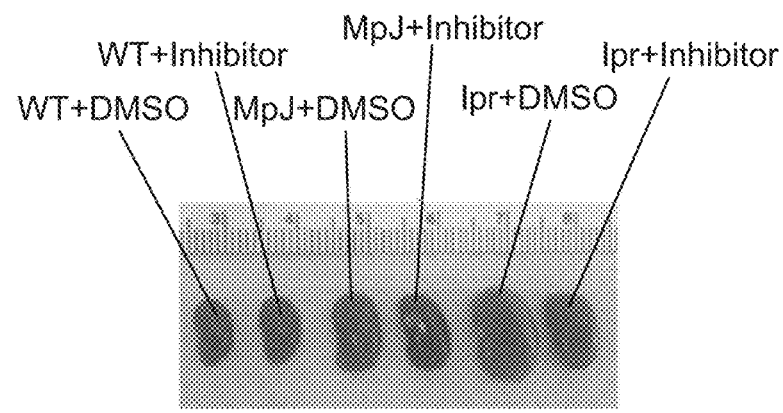
FIGS. 13A & 13B depict the effect of SHP2 inhibition on reducing kidney size and weight in SLE-prone mice, as analyzed in Example 9.
Figure 13B:
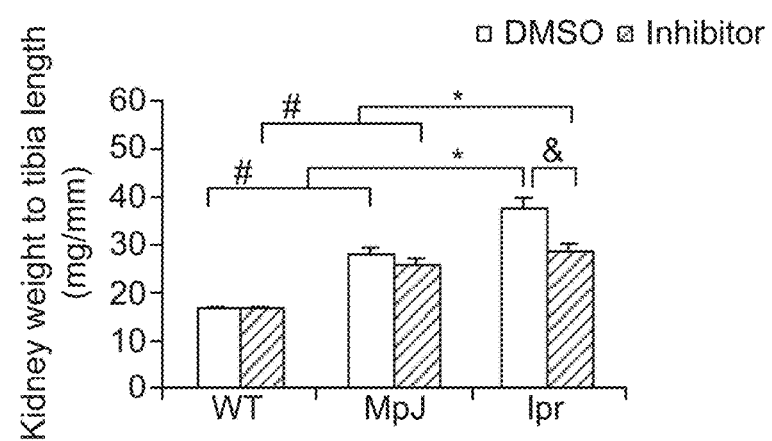

Physiologically, treatment with the SHP2 inhibitor for 6 weeks reduced splenomegaly (FIGS. 12A & 12B) and normalized the kidney to a size (FIGS. 13A & 13B) similar to that in WT and MRL/MpJ controls.

Figure 13C:
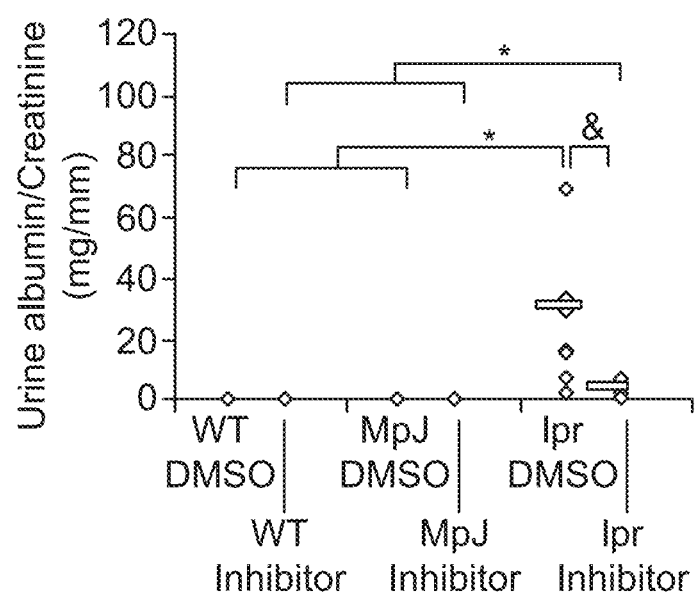
FIG. 13C depicts the effect of SHP2 inhibition on proteinuria, as analyzed in Example 9.

Functionally, the inhibitor-treated mice had a significant reduction in proteinuria (FIG. 13C), with levels similar to those in WT mice, as compared to vehicle-treated SLE mice.

Figure 14G:
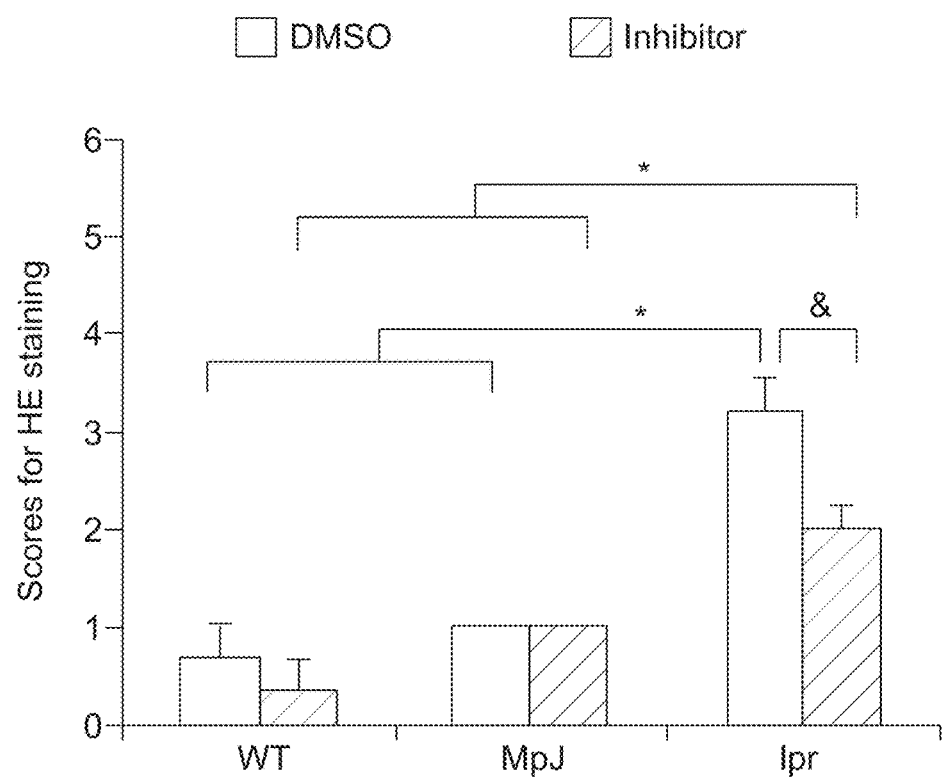
FIG. 14G depicts the unbiased histopathological scoring of SHP2 inhibition in SLE-prone mice, as analyzed in Example 9.
Figure 17A:
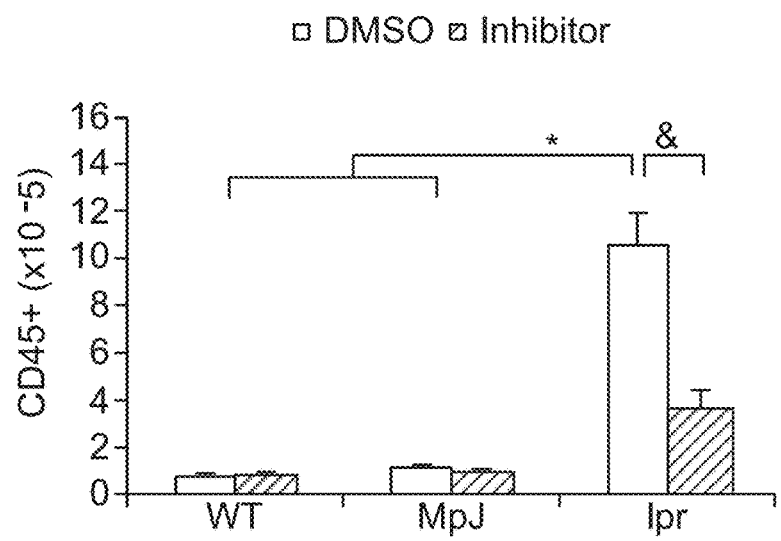
FIGS. 17A-17D depict the effect of SHP2 inhibition on infiltration of cells to the kidney in SLE-prone mice as depicted by decreased numbers of CD45+ and CD3+ cells in SLE treated mice, and show that the effects of the inhibitor decreases the number of CD4+, CD8+, and double-negative T cells, as well as the numbers of neutrophils and macrophages that infiltrate into the kidney in SLE, as analyzed in Example 10.
Figure 17B:
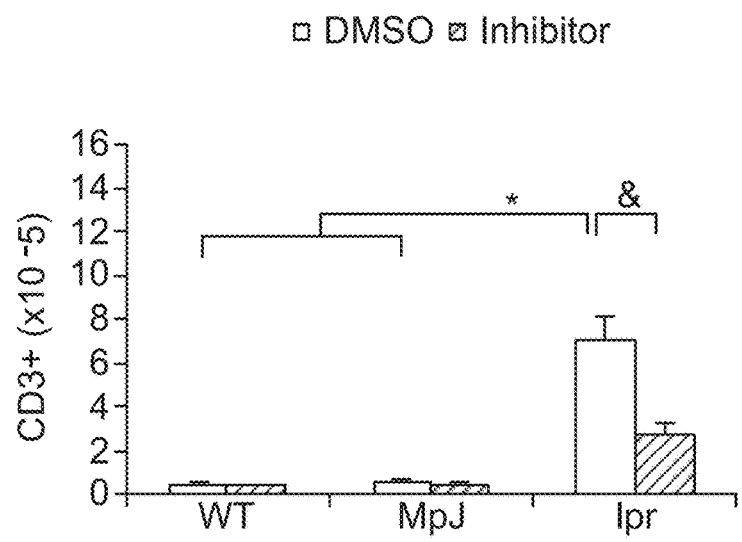
Figure 17C:
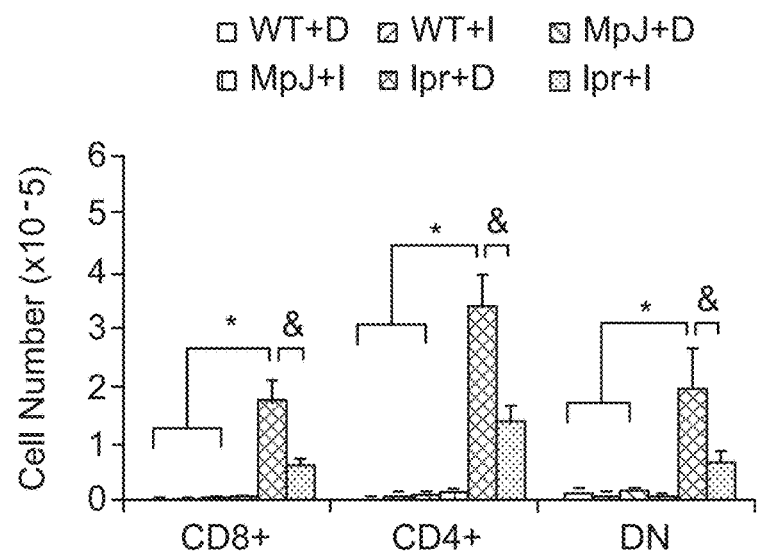
Figure 17D:
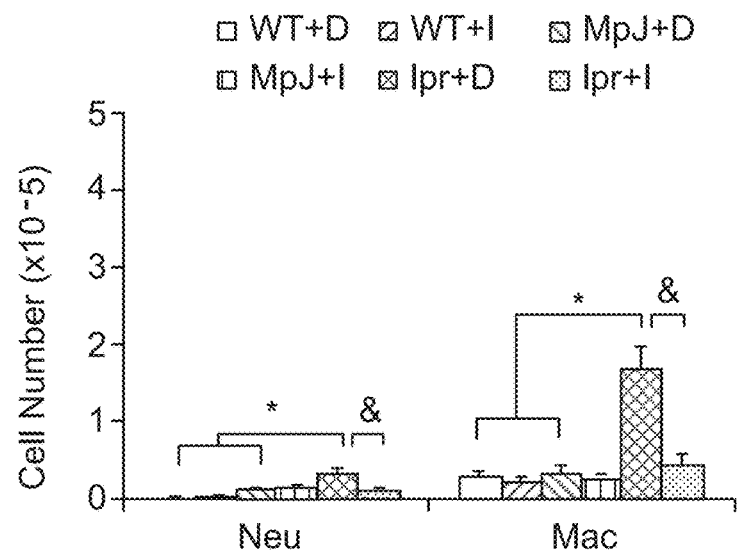

When histologically examining the tissues (FIGS. 14-16), it was observed that the kidneys from MRL/lpr mice treated with vehicle developed severe progressive crescentic glomerulonephritis (FIG. 14C), had significant fibrosis (FIG. 15C), and were infiltrated with immune cells (FIG. 16C). In contrast, treatment of MRL/lpr mice with the SHP2 inhibitor prevented the development of this SLE-related disease phenotype in the kidney of these mice (FIGS. 14F, 15F and 16F). Unbiased histopathological scoring indicated that treatment of MRL/lpr mice with the SHP2 inhibitor quantifiably prevented the development of SLE-related disease phenotype in the kidney of these mice (FIG. 14G). As shown in FIGS. 16E-16F, PAS staining of tissue showed decreased inflammatory infiltration in the tissue, smaller glomeruli, decreased fibrosis, and decreased numbers of mesangial cells surrounding the glomerulus in SLE kidneys treated with SHP2 inhibitor.

Example 10

In this Example, the effect of L97M74 on SHP2 activity on cellular immune response in kidney was evaluated.

B cells, T cells, macrophage and neutrophils from the MRL/lpr inhibitor-treated and vehicle-treated mouse kidneys of Example 9 were isolated.

As shown in FIGS. 17A-17D, it was found that the SHP2 inhibitor specifically targeted the total number of infiltrating T cells in the SLE kidney, significantly reducing the overall number of CD4, CD8, and double-negative T cells in inhibitor-treated SLE mice as compared to vehicle-treated mice. Unexpectedly, no discernable differences in B cells were observed. In addition, a significant reduction in numbers of infiltrating neutorophils and macrophages in inhibitor-treated SLE kidneys were also observed.

Example 11

In this Example, the effect of L97M74 on SHP2 activity on cellular immune response in spleen was evaluated.

B cells, T cells, macrophage and neutrophils from spleens obtained from the MRL/lpr inhibitor-treated and vehicle-treated mice of Example 9 were isolated.

Figure 19A:
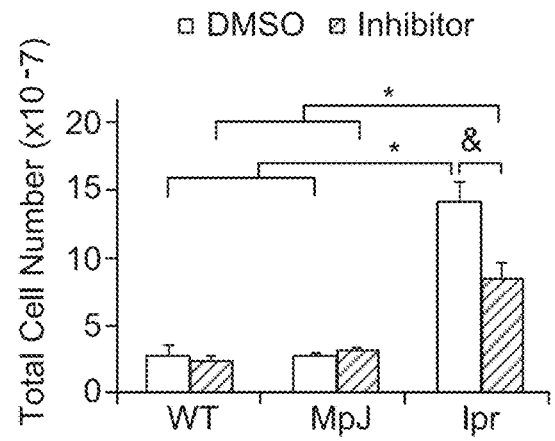
FIGS. 19A-19C depict the effect of SHP2 inhibition on total immune cell numbers in the spleen of SLE-prone mice and show that the effects of the inhibitor decreases the number T cells specifically; in addition, effects of the inhibitor on of reducing the numbers of cytotoxic CD4+, CD8+, and double-negative T cells, but not the number of regulatory T cells (CD4+CD25+), is also shown, as analyzed in Example 11.
Figure 19B:
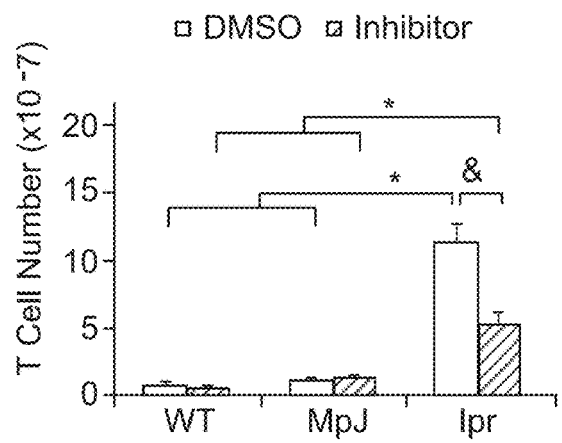
Figure 19C:
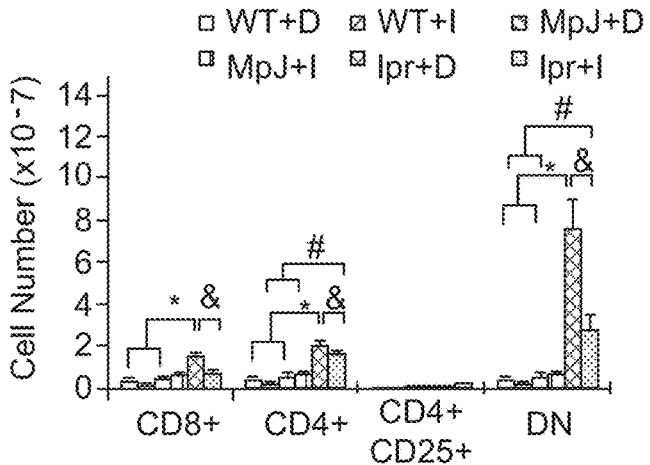

Similar to the results in Example 10, germinal center formation in the spleen was greatly reduced in the SHP2 inhibitor-treated MRL/lpr mice, as compared to MRL/lpr vehicle-treated, and resembled splenic histology similar to that observed in the WT and MRL/MpJ controls (FIGS. 18A-18D). Like the kidney in mice treated with the inhibitor in Example 10, overall splenic T cell counts were reduced in the MRL/lpr inhibitor-treated mice, with significant reduction in CD4, CD8, and double-negative T cells, but not CD25 helper T cell populations (FIGS. 19A-19C).

Figure 20A:
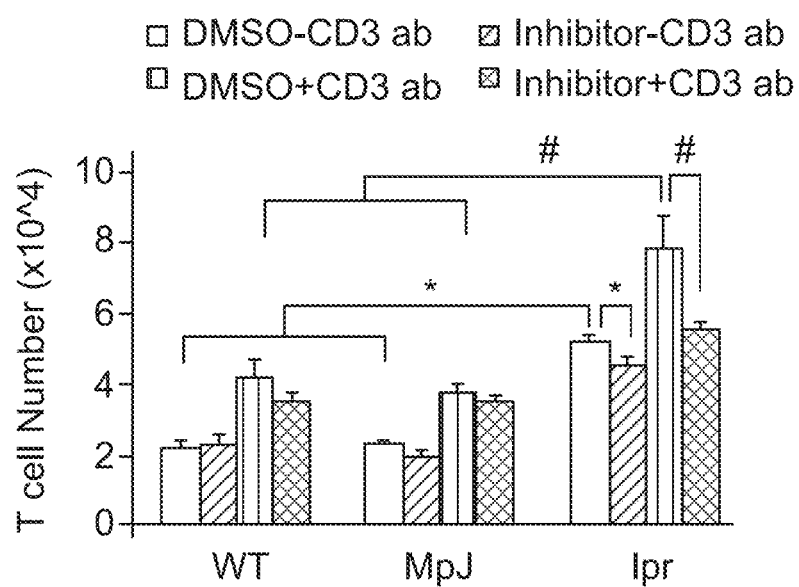
FIG. 20A depicts that SHP2 inhibition decreases proliferation of cultured T cells isolated from the spleen of SLE-prone mice, as shown through a reduction in total T cell number, both in the absence or presence of T-cell activation (CD3 antibody), as analyzed in Example 11.
Figure 20B:
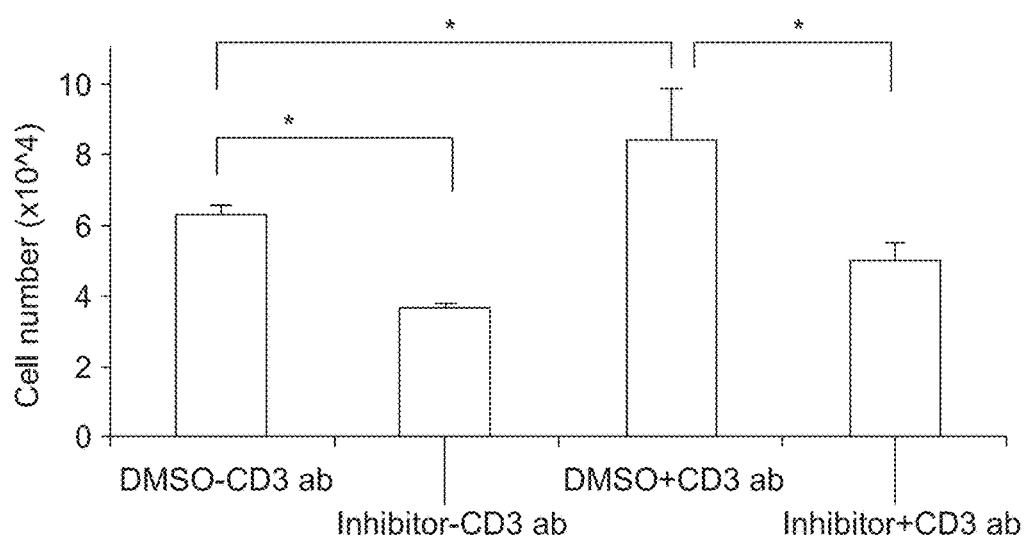
FIG. 20B depicts that SHP2 inhibitor decreases proliferation of tissue-cultured double-negative T cells isolated from spleen of SLE-prone mice, as shown through a reduction in total double-negative T cell number, both in the absence or presence of CD3 activation (CD3 ab), as analyzed in Example 11.
Figure 21A:
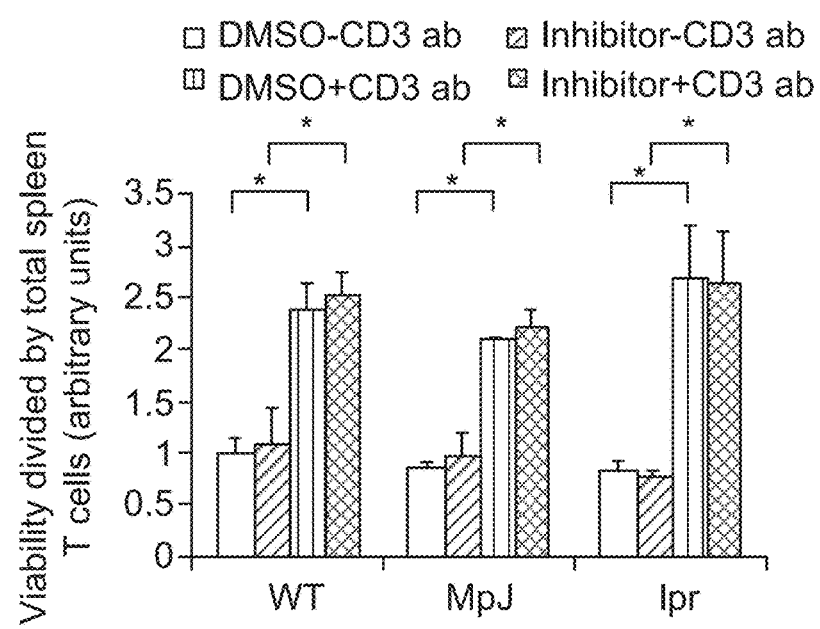
FIG. 21A depicts that SHP2 inhibition has no effect on total T cell viability in cultured T cells isolated from the spleen of SLE-prone mice, both in the absence or presence of T-cell activation (CD3 antibody), as analyzed in Example 11.
Figure 21B:
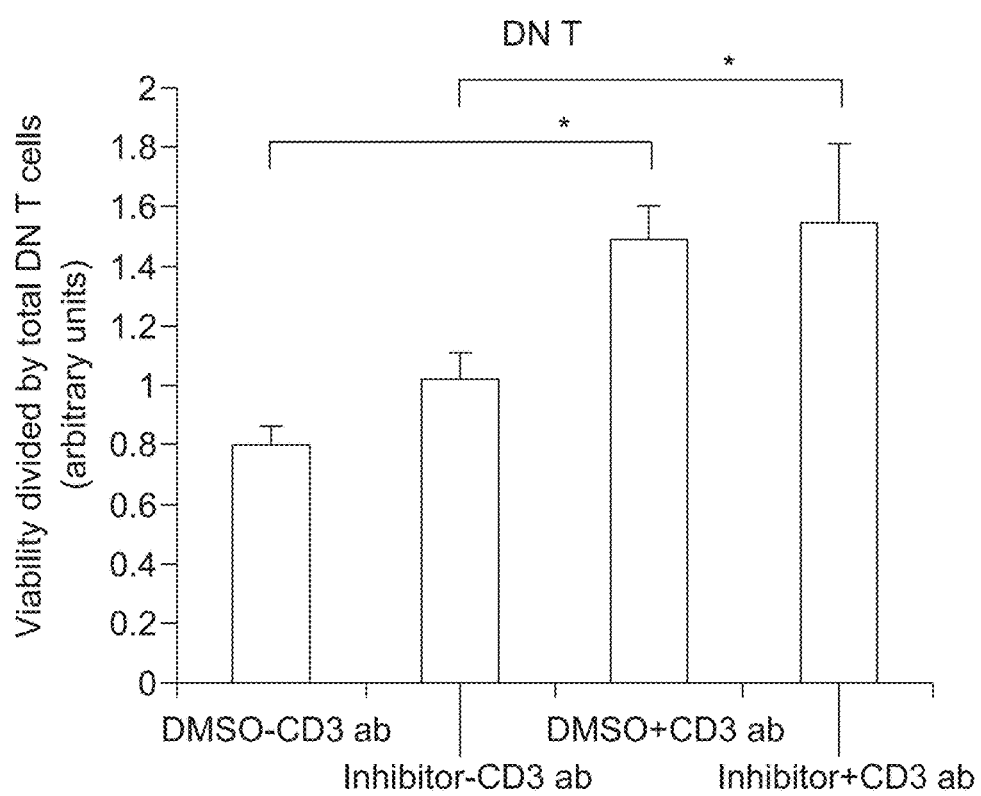
FIG. 21B depicts that SHP2 inhibitor does not affect viability of tissue-cultured double-negative T cells, both in the absence or presence of CD3 activation (CD3 ab), as analyzed in Example 11.
Figure 22A:
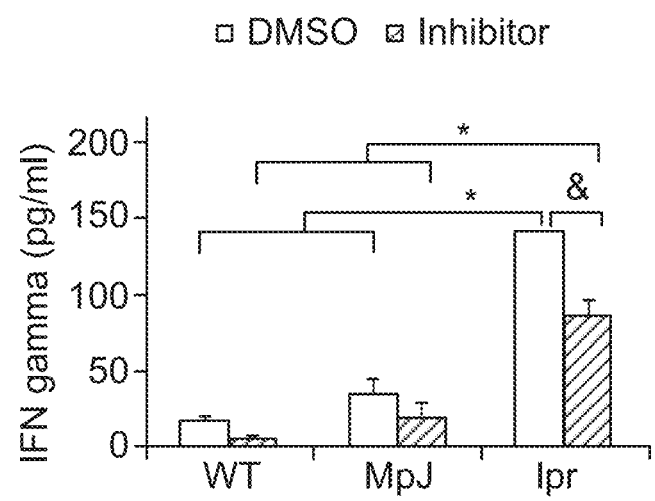
FIGS. 22A-22D depict the effect of SHP2 inhibition on levels of circulating cytokines in serum isolated from in SLE-prone mice, as analyzed in Example 12.
Figure 22B:
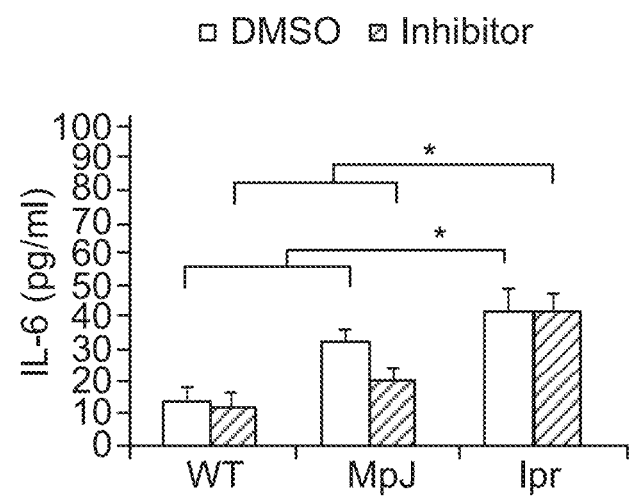
Figure 22C:
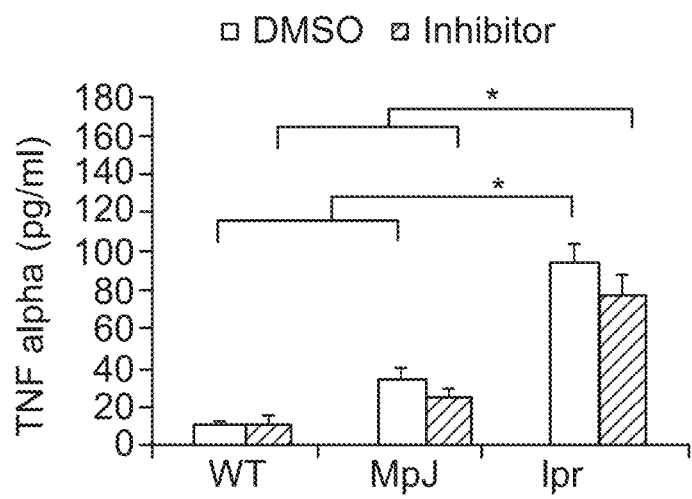
Figure 22D:
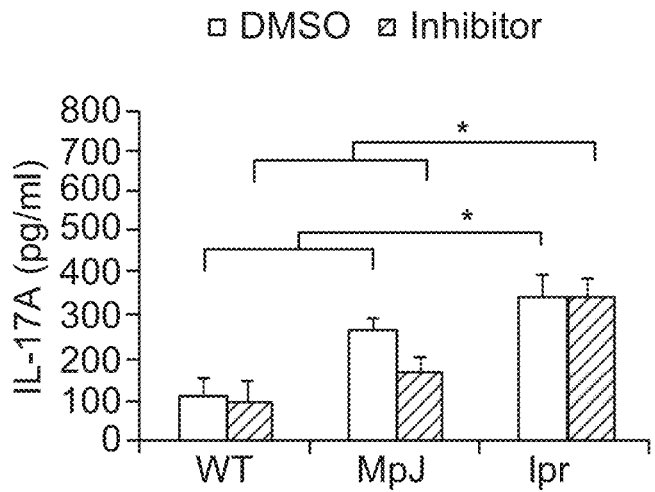

Additionally, to determine specifically whether the inhibitor affects active or inactive T cells, the T cell population from the spleen of MRL/lpr inhibitor-treated or vehicle-treated mice were isolated and cultured and either left unstimulated or stimulated with CD3 to active the T cells for 48 hours. Unexpectedly, both inactive and CD3 activated T cell proliferation was significantly inhibited by the SHP2 inhibitor in the SLE mice. Moreover, the proliferative effects observed were specific to the double-negative T cell population (FIG. 20A). SHP2 inhibitor decreased the total number of double-negative T cells upon CD3 activation in MRL/lpr spleens (FIG. 20B). No effects were observed in WT or MRL/MpJ control cells either in the presence or absence of stimulation or in response to the inhibitor. SHP2 inhibition had no effect on total T cell viability in cultured T cells isolated from the spleen of SLE-prone mice, both in the absence or presence of T-cell activation (CD3 antibody) (FIG. 21A). SHP2 inhibitor also did not affect viability of tissue-cultured double-negative T cells, both in the absence or presence of CD3 activation (CD3 ab) (FIG. 21B).

In summary, SHP2 inhibition reduces the number of splenic lymphocytes, particularly CD4+, CD8+ and DN T cells, and reduces infiltration of CD4 and double-negative T cells to kidney, suggesting that normalization of SHP2 activity in T cells specifically may significantly inhibit organ damage associated with SLE.

Example 12

In this Example, the effect of the SHP2 inhibitor (L97M74) on specific cytokines to drive downstream activation of pathways that lead to SLE pathogenesis was evaluated.

An ELISA was conducted to detect concentrations of IFNγ, TNFα, IL17, and IL6 in T cells derived from spleen.

Interestingly, as shown in FIGS. 22A-22D, only significant decreases in IFNγ were observed in response to the SHP2 inhibitor. No effects on TNFα, IL17 or IL6 were observed in response to the SHP2 inhibitor, despite the fact that these cytokines were significantly increased in SLE, suggesting that the SHP2 inhibitor specifically ameliorates the pathogenic effects of SLE through specific inhibition of double-negative T cells and production of IFNγ.

Example 13

In this Example, the effect of the SHP2 inhibitor on thymus size was evaluated.

Figure 23:
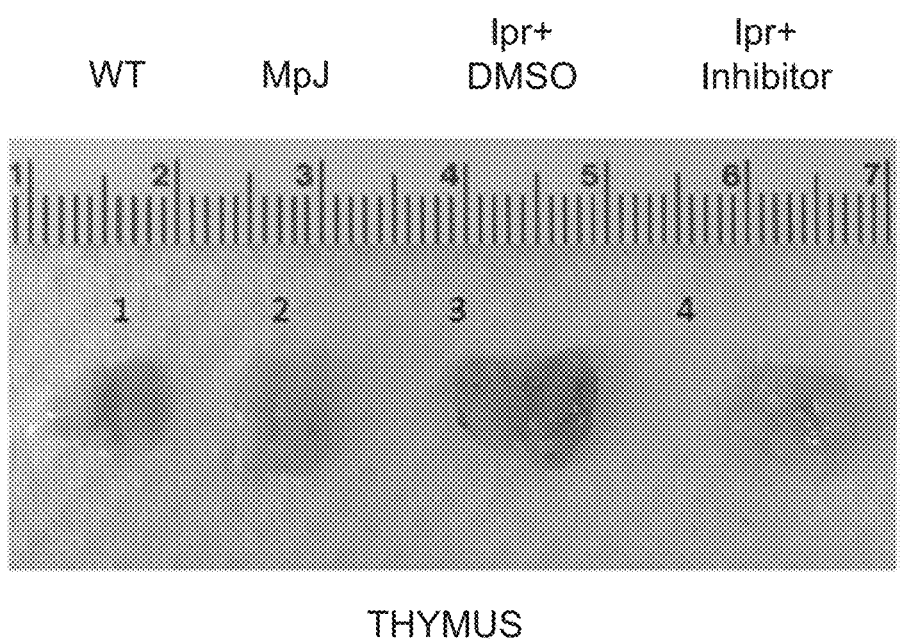
FIG. 23 depicts the effect of SHP2 inhibition on thymus size in SLE-prone mice, as analyzed in Example 13.

As shown in FIG. 23, inhibition of SHP2 decreased thymus size in SLE-prone mice.

Example 14

In this Example, the effect of the SHP2 inhibitor (L97M74) on cardiac function was evaluated.

Figures 24A, 24B:
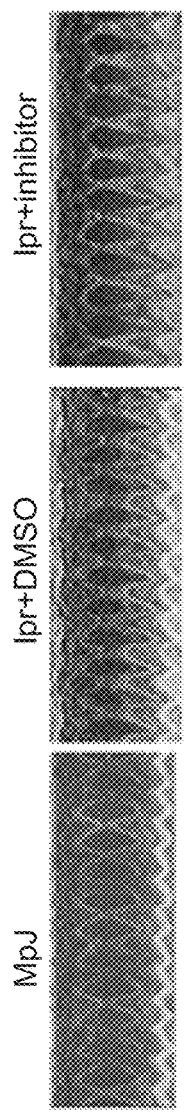
FIG. 24A depicts the effect of SHP2 inhibition on cardiac function as assessed by echocardiography, as analyzed in Example 14.
FIG. 24B depicts the quantified effects of SHP2 inhibition on cardiac function of control vs. SLE-prone hearts, as assessed by left ventricular chamber dimension, posterior wall thickness, and fractional shortening, as analyzed in Example 14.

Hearts from SHP2 inhibitor-treated mice showed significantly improved functional parameters as compared to vehicle-treated SLE mice (FIG. 24A), with decreased chamber and increased posterior wall measurements (FIG. 24B), and similar to MRL/MpJ control hearts.

Example 15

Figure 25A:
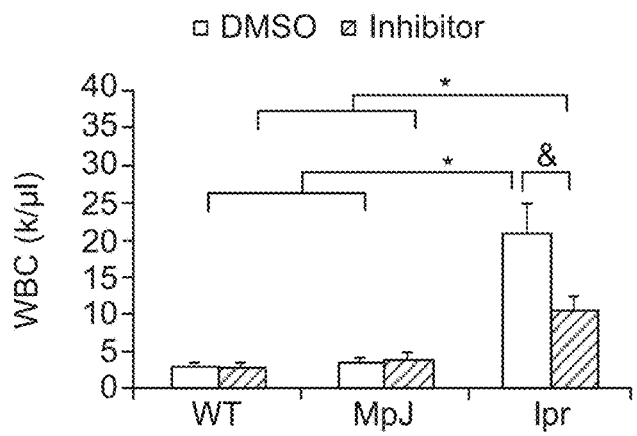
FIGS. 25A-25C depict the effect of SHP2 inhibition on circulating cell numbers in serum isolated from control or SLE-prone mice, as analyzed in Example 15.
Figure 25B:
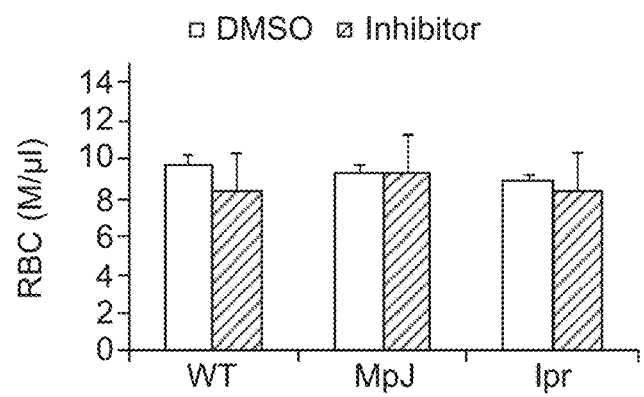
Figure 25C:
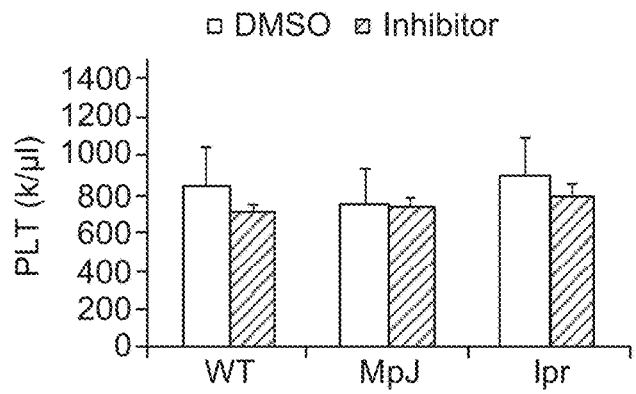
Figure 26A:
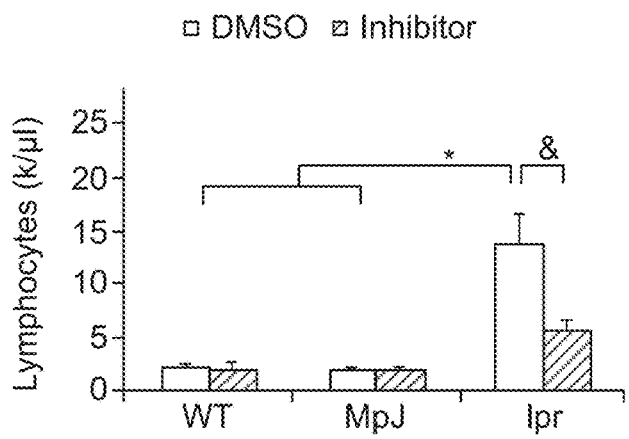
FIGS. 26A-26E depict the effect of SHP2 inhibition on circulating levels of the subsets of white blood cells in serum isolated from control or SLE-prone mice, as analyzed in Example 15.
Figure 26B:
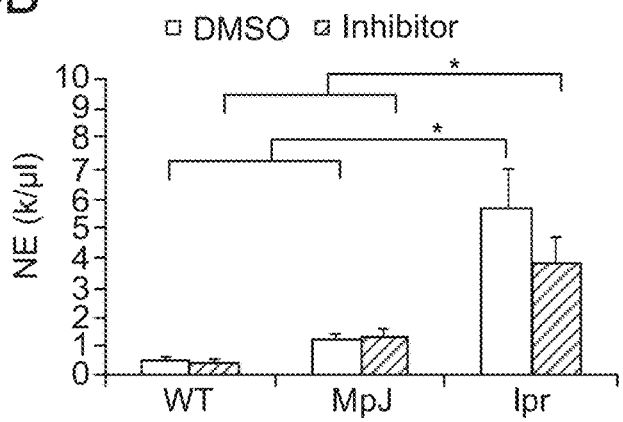
Figure 26C:
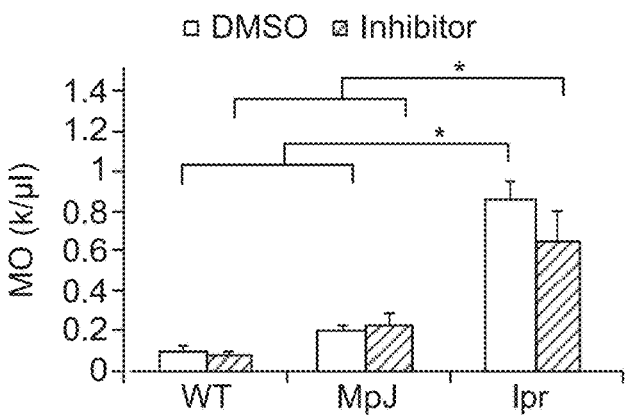
Figure 26D:
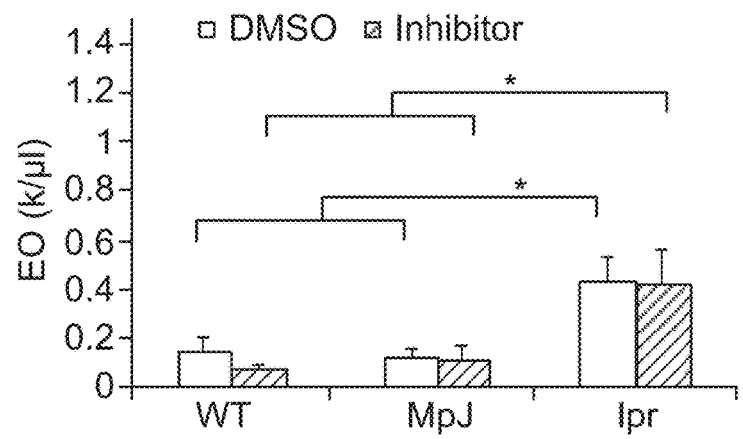
Figure 26E:
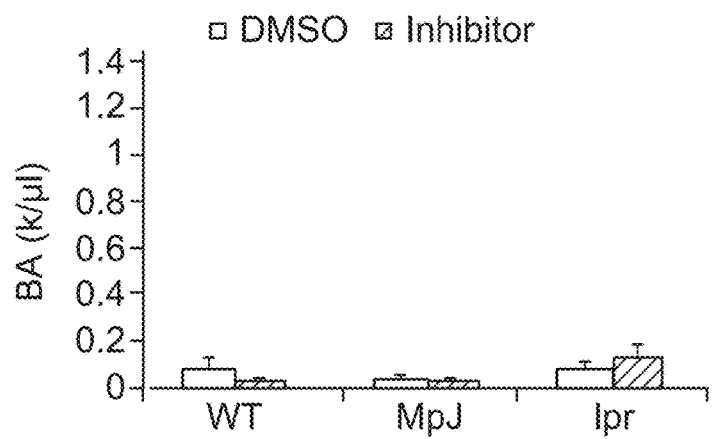

In this Example, the effect of the SHP2 inhibitor (L97M74) in mediating the immune response to elicit the SLE pathogenic response was evaluated The serological immune response in SLE inhibitor-treated versus SLE vehicle-treated mice were assessed and found that the SHP2 inhibitor specifically targets the white blood cell (WBC) population, with no effects observed in red blood cells or platelets (FIGS. 25A-25C). Of these WBCs, only leukocytes, but not neutrophils, monocytes, eosinophils, or basophils, were significantly reduced by the SHP2 inhibitor (FIGS. 26A-26E).

Figure 27:
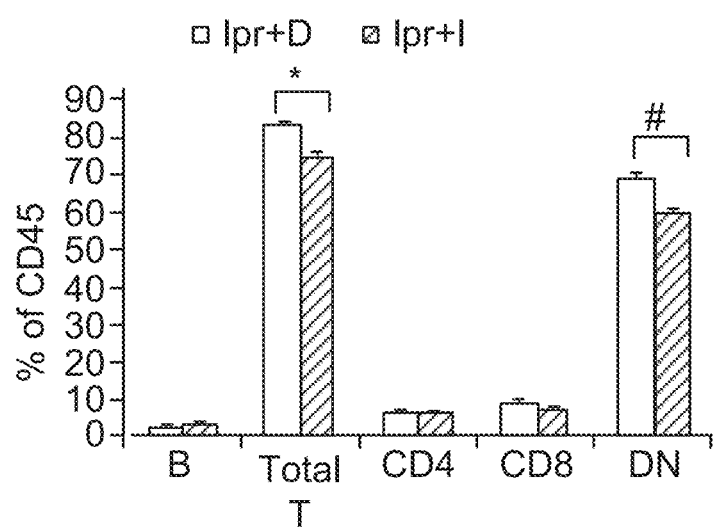
FIG. 27 depicts the effect of SHP2 inhibition on T cell numbers in circulating leukocytes isolated from control or SLE-prone mice, as analyzed in Example 15.

As shown in FIG. 27, it was further determined that only the T cell, and not the B cell, leukocyte population was significantly altered in SLE and inhibited by the SHP2 inhibitor. Moreover, of the T cell population, only the double negative cells, and not the CD4 and CD8 positive T cell populations, were targeted by the SHP2 inhibitor in circulating lymphocytes, suggesting specificity in regulating SLE pathogenesis through this specific immune cell subset.

Figure 28:
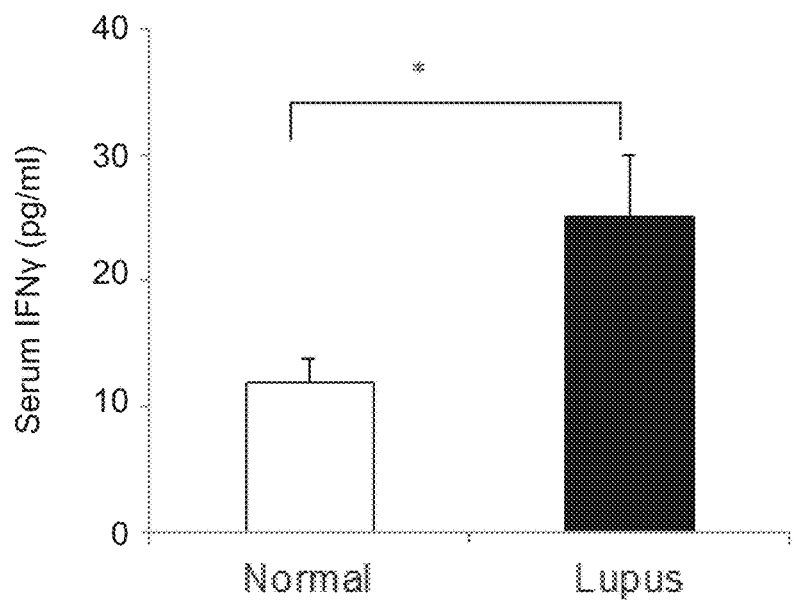
FIG. 28 depicts the effect of SHP2 inhibition on IFNγ levels in serum from normal and SLE-disease active human patients, as analyzed in Example 15.

Additionally, to assess if cytokine effects are similarly affected in human SLE, IFNγ in serum of normal SLE-disease active patients was measured. Like in mice, a significant increase in IFNγ levels in SLE patient serum was observed (FIG. 28).

Because of these results, if/how SHP2 was similarly involved in mediating the immune response in human SLE pathogenesis was next evaluated. To determine specifically whether the inhibitor affects human T cells, the T cell population from serum from either normal or SLE-disease active patients was isolated and cultured. Purified T cells were plated and either left unstimulated or stimulated with CD3 to active the T cells for 48 hours.

Figure 29:
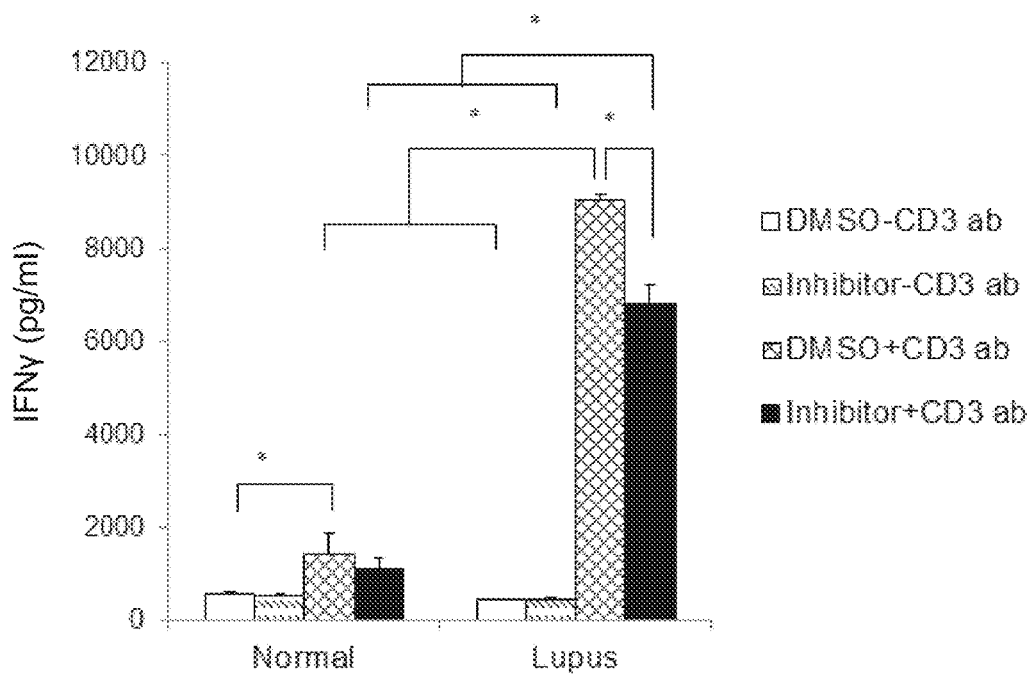
FIG. 29 depicts the effect of SHP2 inhibition on IFNγ activity in response to T cell activation (with CD3 ab) in serum from normal and SLE-disease active human patients, as analyzed in Example 15.
Figure 30A:
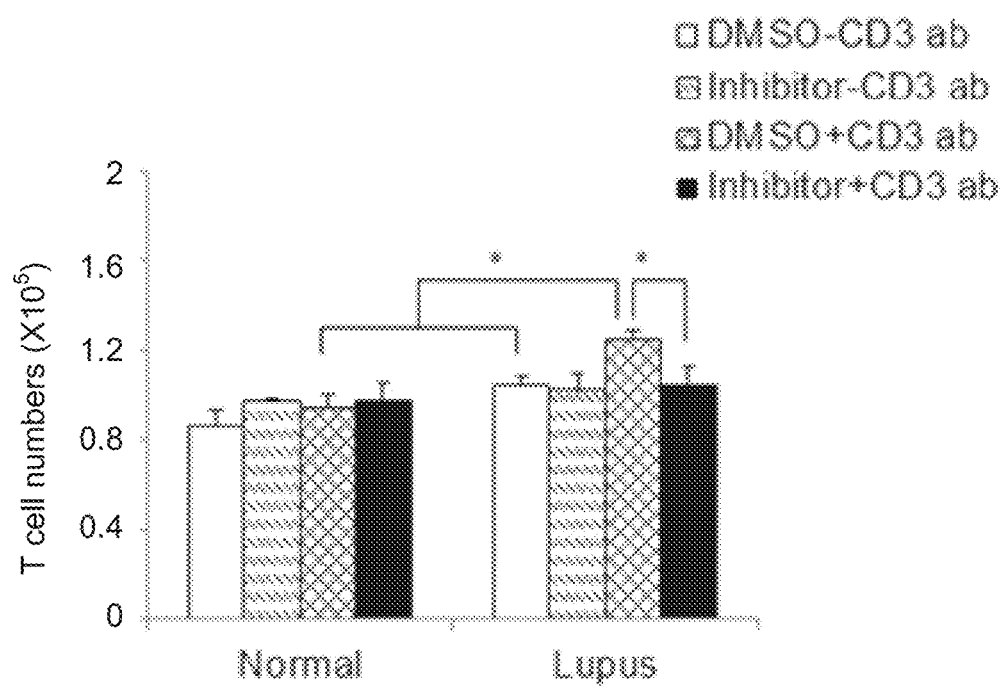
Figure 31:
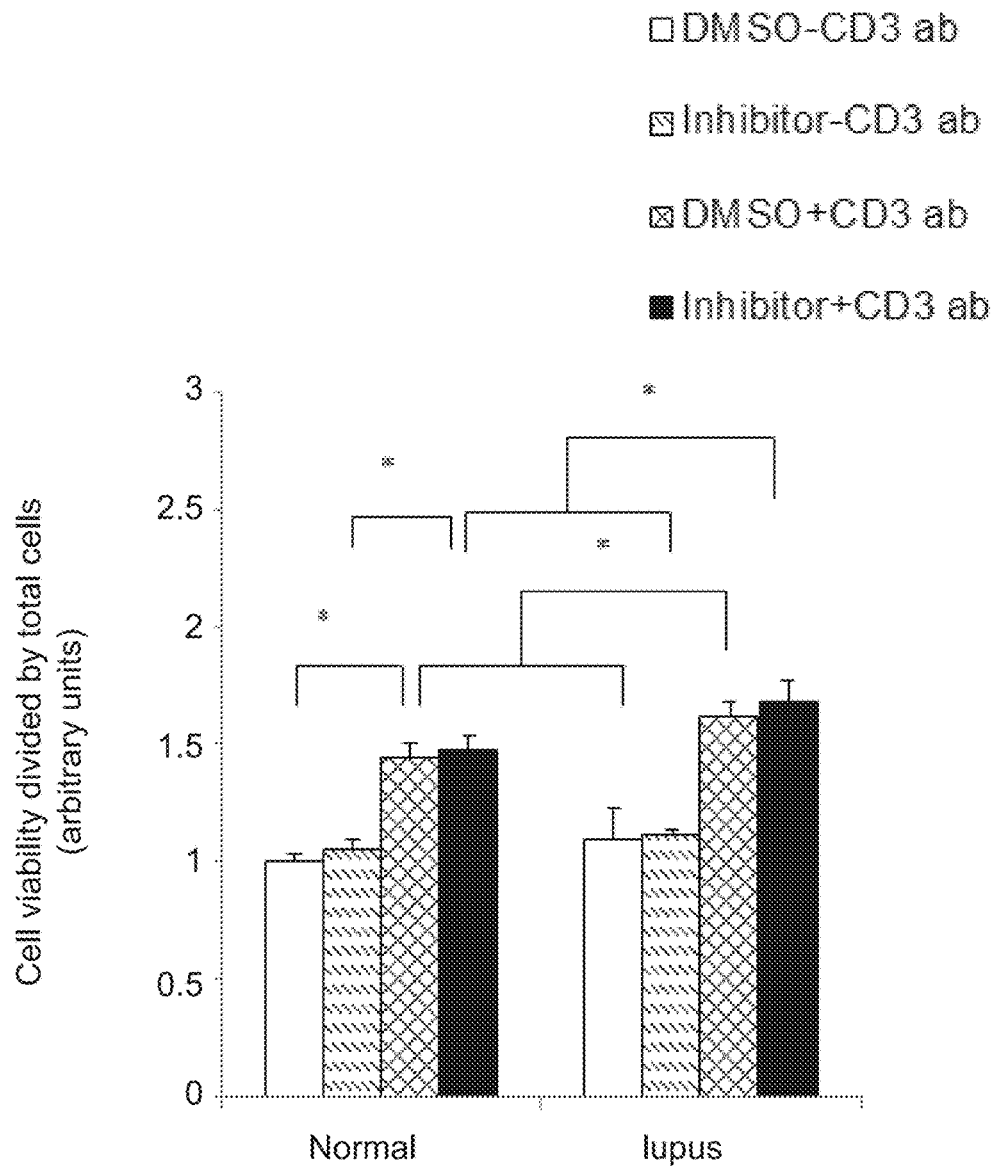
FIG. 31 depicts that SHP2 inhibition does not exert its effects by reducing T cell viability in human SLE cultures, as analyzed in Example 15.

Cultured human T cells isolated from SLE patients secreted more IFNγ upon activation by CD3 antibody; however, the SHP2 inhibitor significantly decreased the secretion of IFNγ activity in response to T cell activation (FIG. 29). Moreover, inhibition of SHP2 reduced T cell proliferation in response to CD3 in culture (FIG. 30A), as shown by a decrease in T cell clonal expansion in SHP2 inhibitor-treated human SLE T cells compared to vehicle-treated human SLE T cells (FIG. 30B). Like in the isolated mouse T cell cultures, the SHP2 inhibitor prevented T cell proliferation in response to CD3 activation directly, as no differences in viability (i.e. apoptosis) were observed (FIG.

31). Thus, SHP2 inhibitor does not inhibit T cell viability and reduce the number of T cells in SLLE through increased cell death.

Example 16

In this Example, the effect of the SHP2 inhibitor, L97M74, on the onset of SLE disease progression was evaluated by measuring the levels of auto antibodies in SLE inhibitor-treated versus vehicle-treated mice through detection anti-histone antibodies and anti-IgG by ELISA.

Figure 32A:
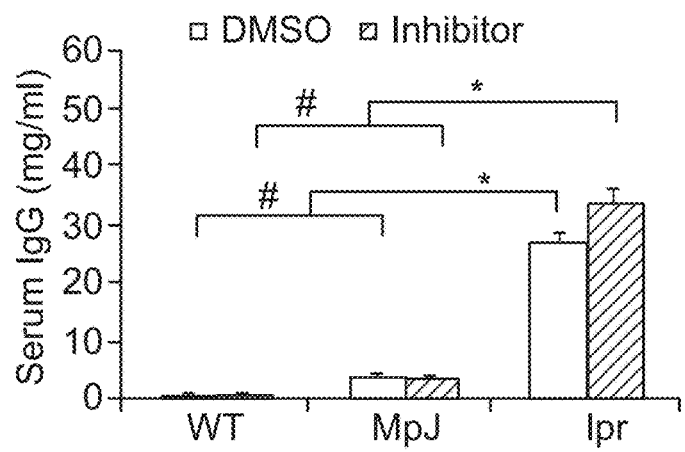
FIGS. 32A & 32B depicts the effect of SHP2 inhibition on serum IgG and anti dsDNA IgG levels, as analyzed in Example 16.
Figure 32B:
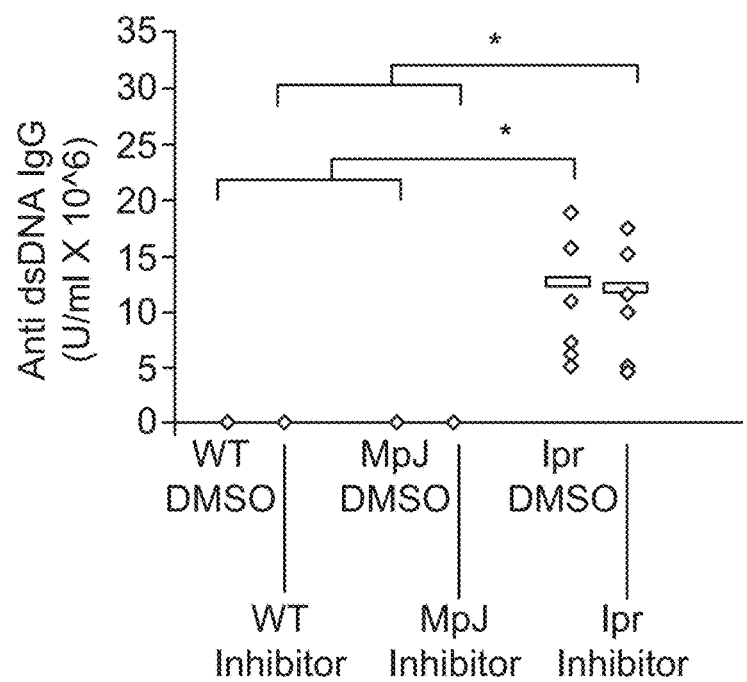

Despite the positive effects of the SHP2 inhibitor in ameliorating the SLE-associated organ damage, levels of IgG and double-stranded DNA were not reduced in SHP2-treated SLE mice, suggesting that the target of the inhibitor is specific to the downstream consequences of SLE disease (FIGS. 32A & 32B).

In summary, these data suggest that increased SHP2 activity, and the aberrant effects this has on downstream cytokine signaling, plays a key role in the molecular pathogenesis of SLE and that use of an SHP2 inhibitor may be a novel therapeutic approach to treating patients for SLE-associated disease pathogenesis.

This written description uses examples to disclose the invention, including the best mode, and also to enable any person skilled in the art to practice the invention, including making and using any systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for inhibiting specific oncogenic Src homology-2 domain containing protein tyrosine phosphatase-2 (SHP2) phosphatase activity, the method comprising administering to a subject in need thereof a specific oncogenic Src homology-2 domain containing protein tyrosine phosphatase-2 (SHP2) inhibitor having the formula (I):

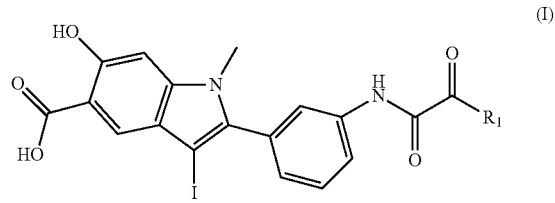

(I)

wherein $R_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

2. The method of claim 1 wherein the SHP2 inhibitor has the formula selected from the group consisting of

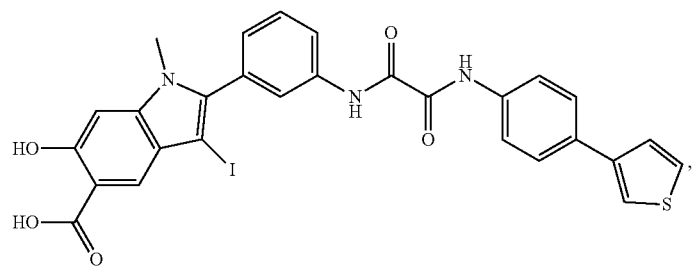
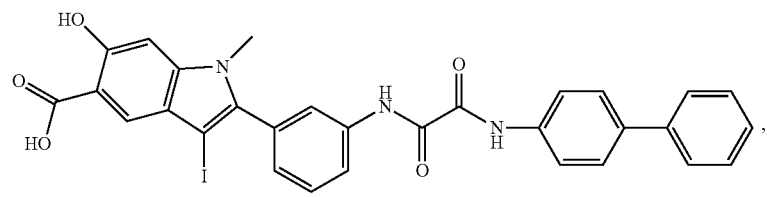
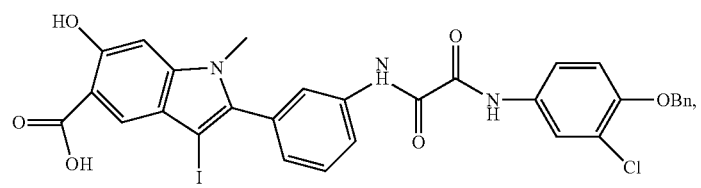
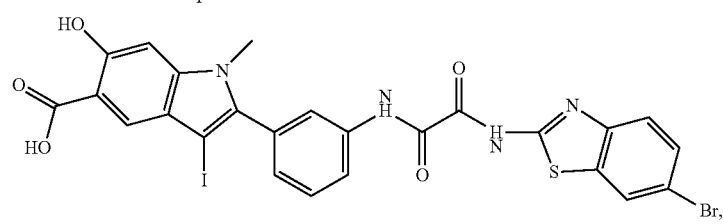
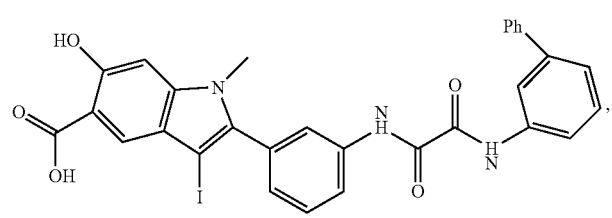
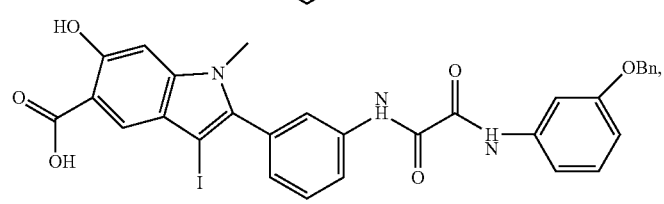
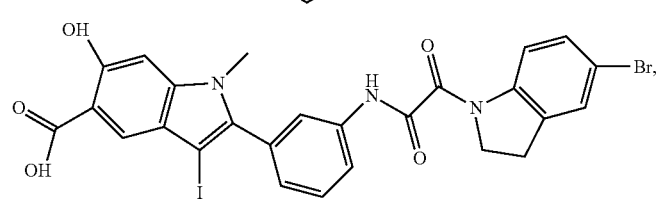
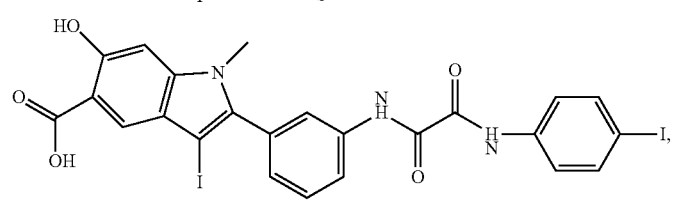

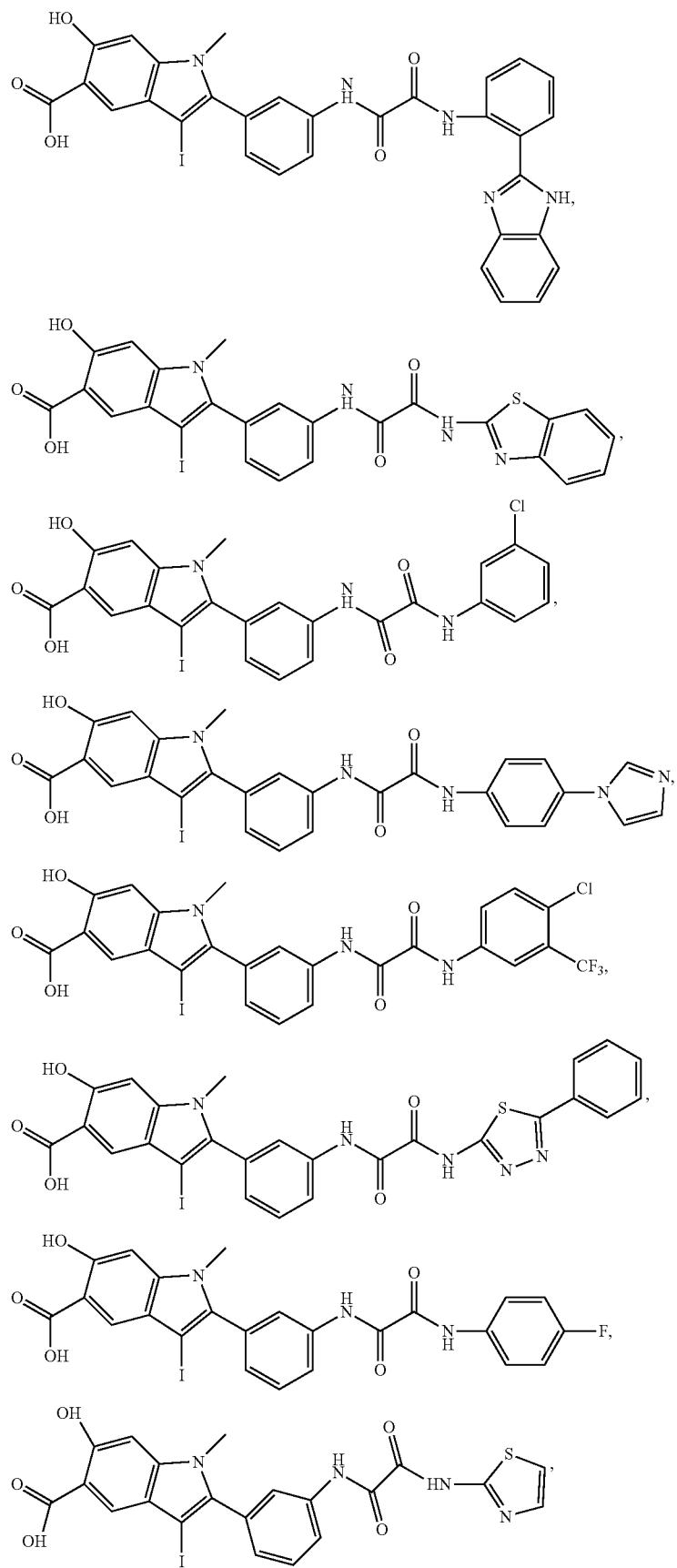

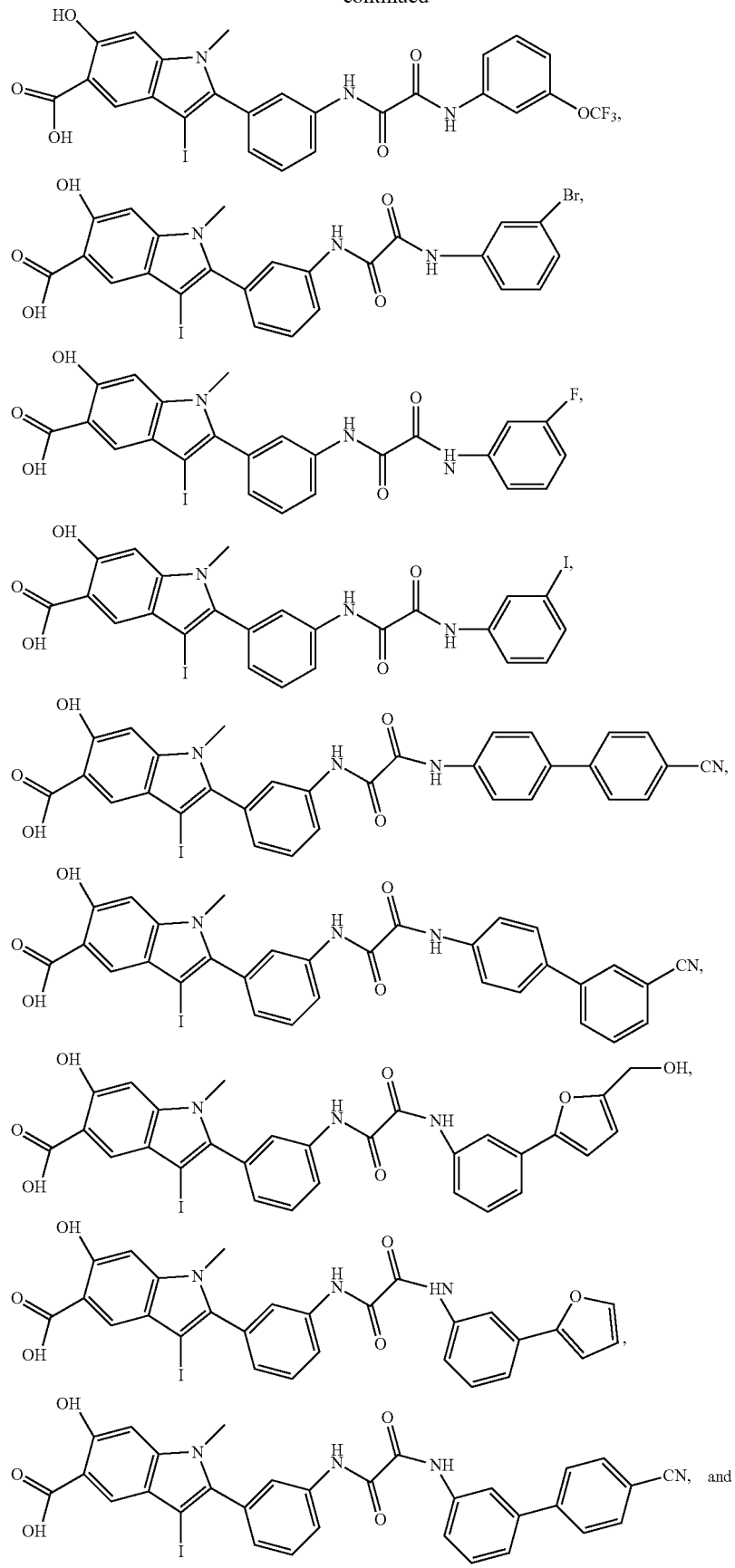

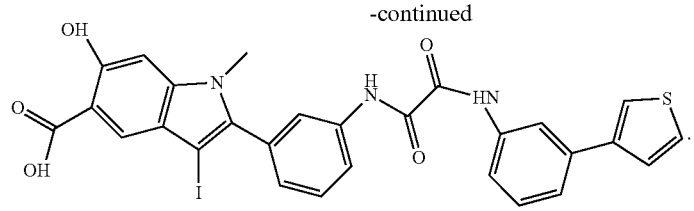

3. The method of claim 1 wherein the SHP2 inhibitor is administered using an administration route selected from the group consisting of: oral (po), intravenous (iv), intramuscular (im), subcutaneous (sc), parenteral, transdermal, inhalation, buccal, ocular, sublingual, vaginal, rectal, and combinations thereof.

4. The method of claim 1 wherein the SHP2 inhibitor is administered in an amount ranging from about 1 mg/Kg body weight/day to about 25 mg/Kg body weight/day.

5. The method of claim 1 wherein the SHP2 inhibitor is administered in an amount ranging from about 5 mg/Kg body weight/day to about 10 mg/Kg body weight/day.

6. The method of claim 1 wherein the SHP2 inhibitor is administered in an amount of about 7.5 mg/Kg body weight/day.

7. A method for treating glomerulonephritis-associated diseases in a subject in need thereof, the method comprising administering to the subject a specific oncogenic Src homology-2 domain containing protein tyrosine phosphatase-2 (SHP2) inhibitor, wherein the SHP2 inhibitor has the formula (I):

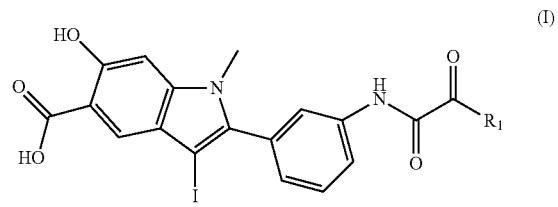

wherein $R_1$=NRaRb, wherein Ra or Rb can each independently be selected from the group consisting of hydrogen, unsubstituted or substituted alkyl, unsubstituted or substituted cycloalkyl, unsubstituted or substituted heterocyclyl, unsubstituted or substituted aryl, unsubstituted or substituted heteroaryl, and unsubstituted or substituted fused 5-12 member aromatic or aliphatic ring system, wherein the substitution on the fused 5-12 member aromatic or aliphatic ring system is selected from the group consisting of nitrogen, oxygen and sulfur.

8. The method of claim 7 wherein the SHP2 inhibitor has the formula selected from the group consisting of

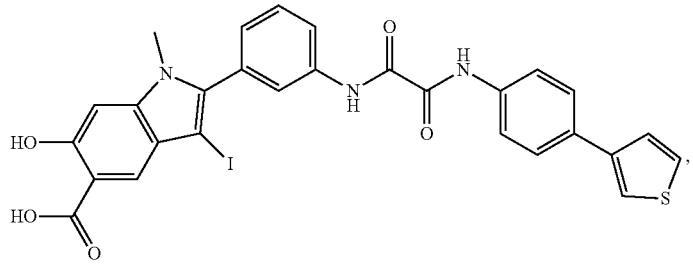

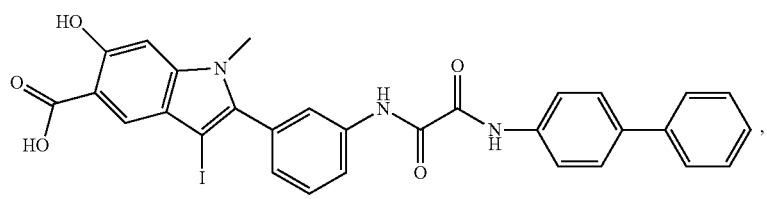

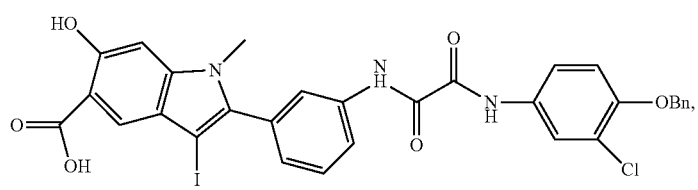

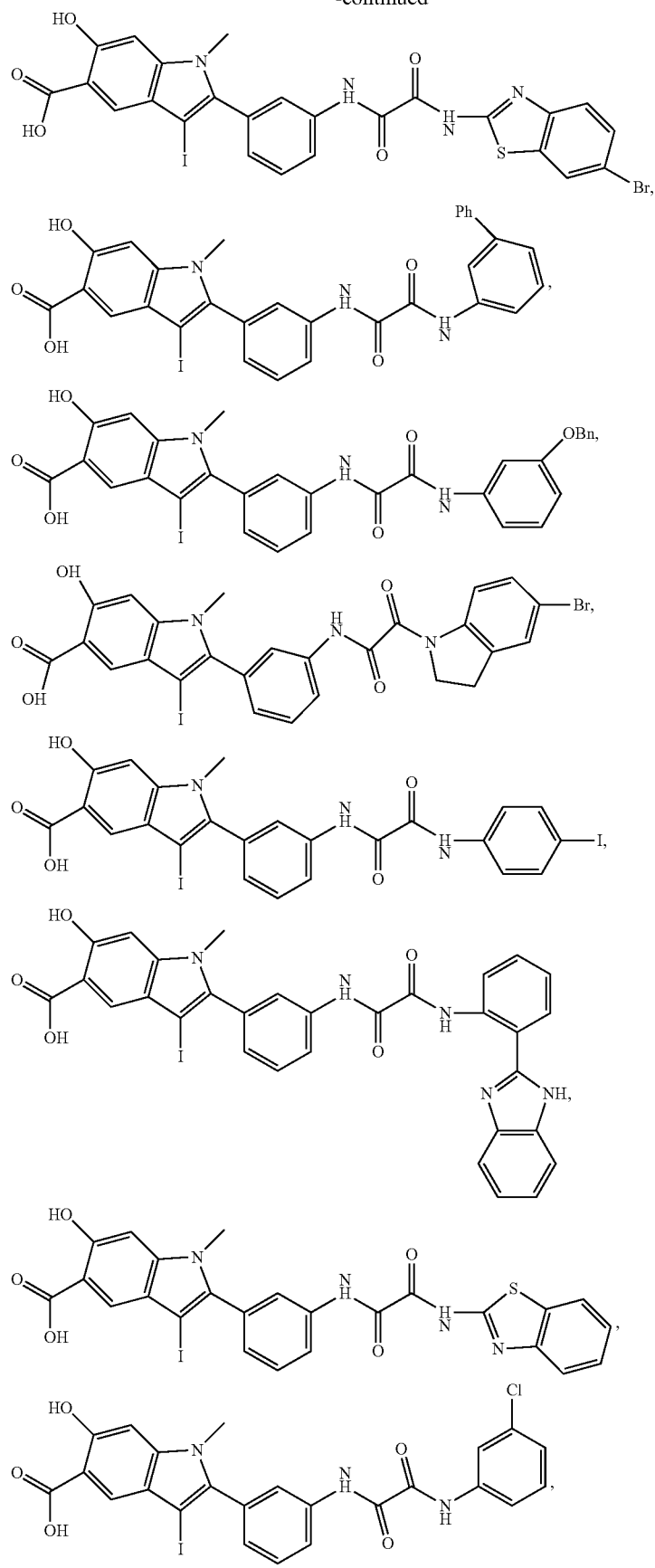

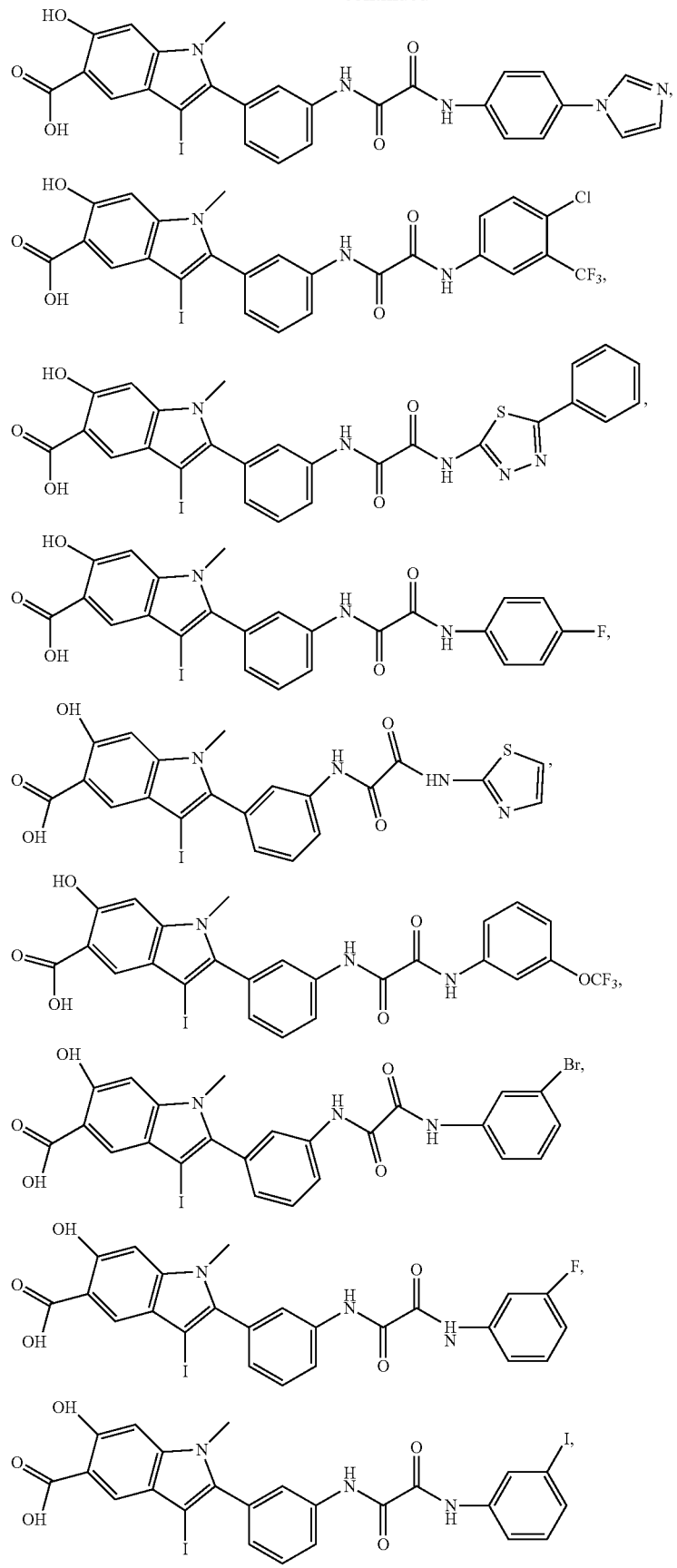

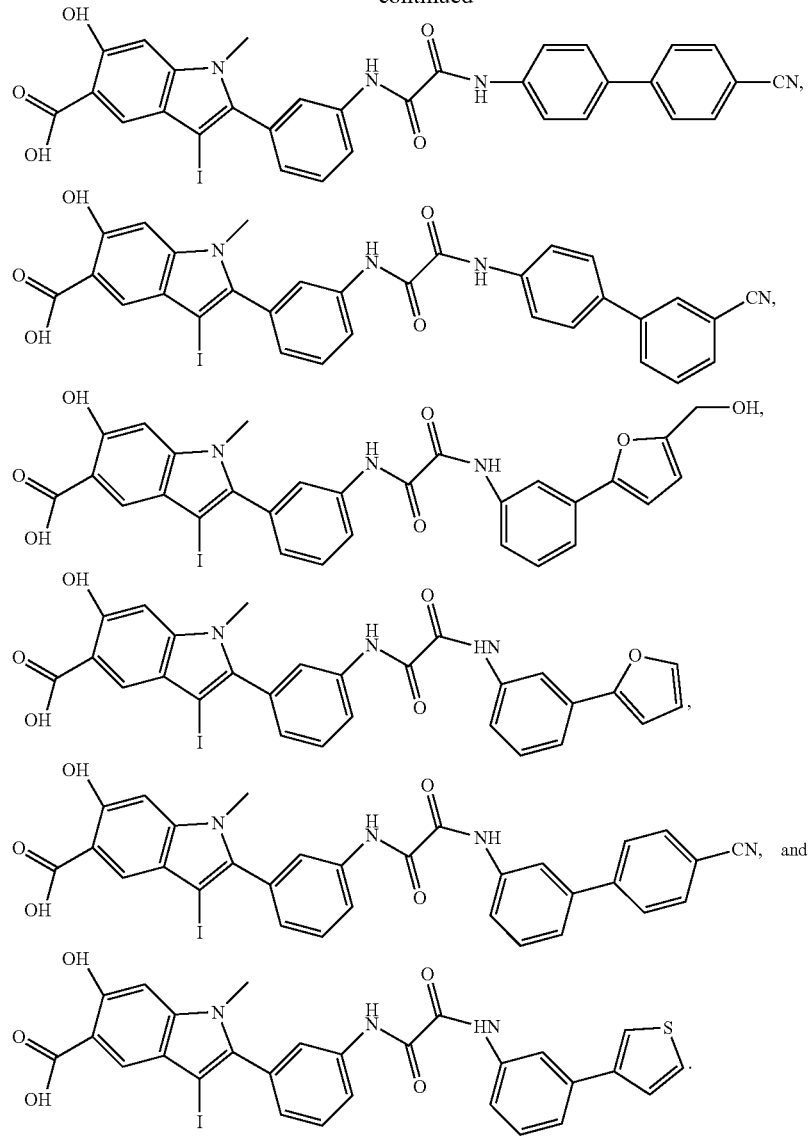

9. The method of claim 8 wherein the SHP2 inhibitor has an $IC_{50}$ value of less than 1 µM.

10. The method of claim 7 wherein the glomerulonephritis-associated disease is selected from the group consisting of postinfectious rapidly progressive glomerulonephritis (RPGN), idiopathic rapidly progressive glomerulonephritis (RPGN), systemic lupus erythematosus (SLE), Goodpasture's syndrome, vasculitis, Wegener's granulomatosis, Henoch-Schonlein purpura, essential cryoglobulinemia, acute proliferative glomerulonephritis, microscopic polyangiitis, Churg-Stauss Syndrome, and IgA neuropathy.

11. The method of claim 7 wherein the SHP2 inhibitor is administered in an amount ranging from about 1 mg/Kg body weight/day to about 25 mg/Kg body weight/day.

12. The method of claim 7 wherein the SHP2 inhibitor is administered in an amount ranging from about 5 mg/Kg body weight/day to about 10 mg/Kg body weight/day.

13. The method of claim 7 wherein the SHP2 inhibitor is administered in an amount of about 7.5 mg/Kg body weight/day.

* * * * *